United States Patent
Stein et al.

(10) Patent No.: US 7,287,995 B2
(45) Date of Patent: Oct. 30, 2007

(54) MEDICAL LEAD AND LEAD CONNECTOR SYSTEM

(76) Inventors: Paul M. Stein, 6876 Timber Crest Dr., Maple Grove, MN (US) 55311; Timothy W. Holleman, 13600 Yancy St., Ham Lake, MN (US) 55303; Andrew J. Ries, 505 S. Glenn Trail, Lino Lakes, MN (US) 55014; Harry Schroder, 2263 Oregon Ct., St. Louis Park, MN (US) 55426; Jordon D. Honeck, 11971 86th Ave. North, Maple Grove, MN (US) 55369; John L. Sommer, 12788 Ibis St. NW., Coon Rapids, MN (US) 55448; Vicki L. Bjorklund, 9056 Rosewood La. North, Maple Grove, MN (US) 55369

( * ) Notice: Subject to any disclaimer, the term of this patent is extended or adjusted under 35 U.S.C. 154(b) by 232 days.

(21) Appl. No.: 10/983,266

(22) Filed: Nov. 8, 2004

(65) Prior Publication Data

US 2005/0065570 A1    Mar. 24, 2005

Related U.S. Application Data

(60) Division of application No. 10/040,143, filed on Jan. 3, 2002, now Pat. No. 6,854,994, which is a continuation-in-part of application No. 09/838,814, filed on Apr. 19, 2001, now Pat. No. 6,705,900.

(60) Provisional application No. 60/270,074, filed on Feb. 21, 2001.

(51) Int. Cl.
*H01R 27/00* (2006.01)

(52) U.S. Cl. ...................................... 439/218; 439/222
(58) Field of Classification Search ................ 439/218, 439/222, 82, 140, 583, 589, 681
See application file for complete search history.

(56) References Cited

U.S. PATENT DOCUMENTS 442,807 A    12/1890    Hatcher (Continued)

FOREIGN PATENT DOCUMENTS

EP    0 587 379 A2    3/1994

(Continued)

*Primary Examiner*—Chandrika Prasad
(74) *Attorney, Agent, or Firm*—Carol F. Barry; Mike C. Soldner; Girma Wolde-Michael

(57) ABSTRACT

A lead connector arrangement includes a non-cylindrically shaped connector pin coupled to a lead conductor and a connector sleeve assembly for receiving the non-cylindrically shaped connector pin. The connector sleeve assembly includes an insert with an axial bore formed therein that complements the shape of the non-cylindrical connector pin. According to one embodiment, the non-cylindrical connector pin may be provided in the form of a triangular, square, rectangular, or hexagonal shape. The axial bore has a complimentary shape to receive the connector pin. When the connector pin is threaded through the connector sleeve assembly using a pull-wire device, the pull-wire device may be unscrewed from the connector pin without causing axial rotation of the lead conductor when the connector pin is fully inserted within the axial bore.

9 Claims, 23 Drawing Sheets

U.S. PATENT DOCUMENTS

| | | |
|---|---|---|
| 3,794,959 A | 2/1974 | Kamolz |
| 3,846,741 A * | 11/1974 | Kunkle et al. ............... 439/82 |
| 4,159,862 A * | 7/1979 | Funck et al. ............... 439/681 |
| 4,274,702 A * | 6/1981 | Buck et al. ............... 439/589 |
| 4,277,126 A * | 7/1981 | Lincoln ............... 439/681 |
| 4,398,783 A * | 8/1983 | Kelly ............... 439/581 |
| 4,411,277 A | 10/1983 | Dickhudt |
| 4,466,441 A | 8/1984 | Skubitz et al. |
| 4,519,234 A * | 5/1985 | Grosse et al. ............... 72/258 |
| 4,583,543 A | 4/1986 | Peers-Travarton |
| 4,628,934 A | 12/1986 | Pohndorf et al. |
| 4,740,170 A | 4/1988 | Lee et al. |
| 4,927,374 A * | 5/1990 | Batty ............... 439/310 |
| 5,000,177 A | 3/1991 | Hoffmann et al. |
| 5,007,864 A | 4/1991 | Stutz |
| 5,050,602 A | 9/1991 | Ospka |
| 5,060,649 A | 10/1991 | Hocherl et al. |
| 5,076,270 A | 12/1991 | Stutz |
| 5,305,666 A * | 4/1994 | LaTorre ............... 81/55 |
| 5,328,442 A | 6/1994 | Levine |
| 5,324,311 A | 7/1994 | Acken |
| 5,374,279 A | 12/1994 | Duffin et al. |
| 5,439,391 A | 8/1995 | McEtchin et al. |
| 5,679,026 A | 10/1997 | Fain et al. |
| 5,697,804 A | 12/1997 | Froberg et al. |
| 5,760,341 A | 6/1998 | Laske et al. |
| 5,766,042 A | 6/1998 | Ries et al. |
| 5,843,141 A | 12/1998 | Bischoff et al. |
| 6,006,135 A | 12/1999 | Kast et al. |
| 6,030,234 A * | 2/2000 | Berg et al. ............... 439/67 |
| 6,044,302 A | 3/2000 | Persuitti et al. |
| 6,295,475 B1 | 9/2001 | Morgan |
| 6,763,270 B1 * | 7/2004 | Gomperz et al. ............ 607/126 |

FOREIGN PATENT DOCUMENTS

| | | |
|---|---|---|
| EP | 0442 807 | 5/1998 |
| WO | WO 00/64535 | 11/2000 |
| WO | WO 01/80941 A2 | 11/2001 |
| WO | WO 02/068050 A1 | 9/2002 |

* cited by examiner

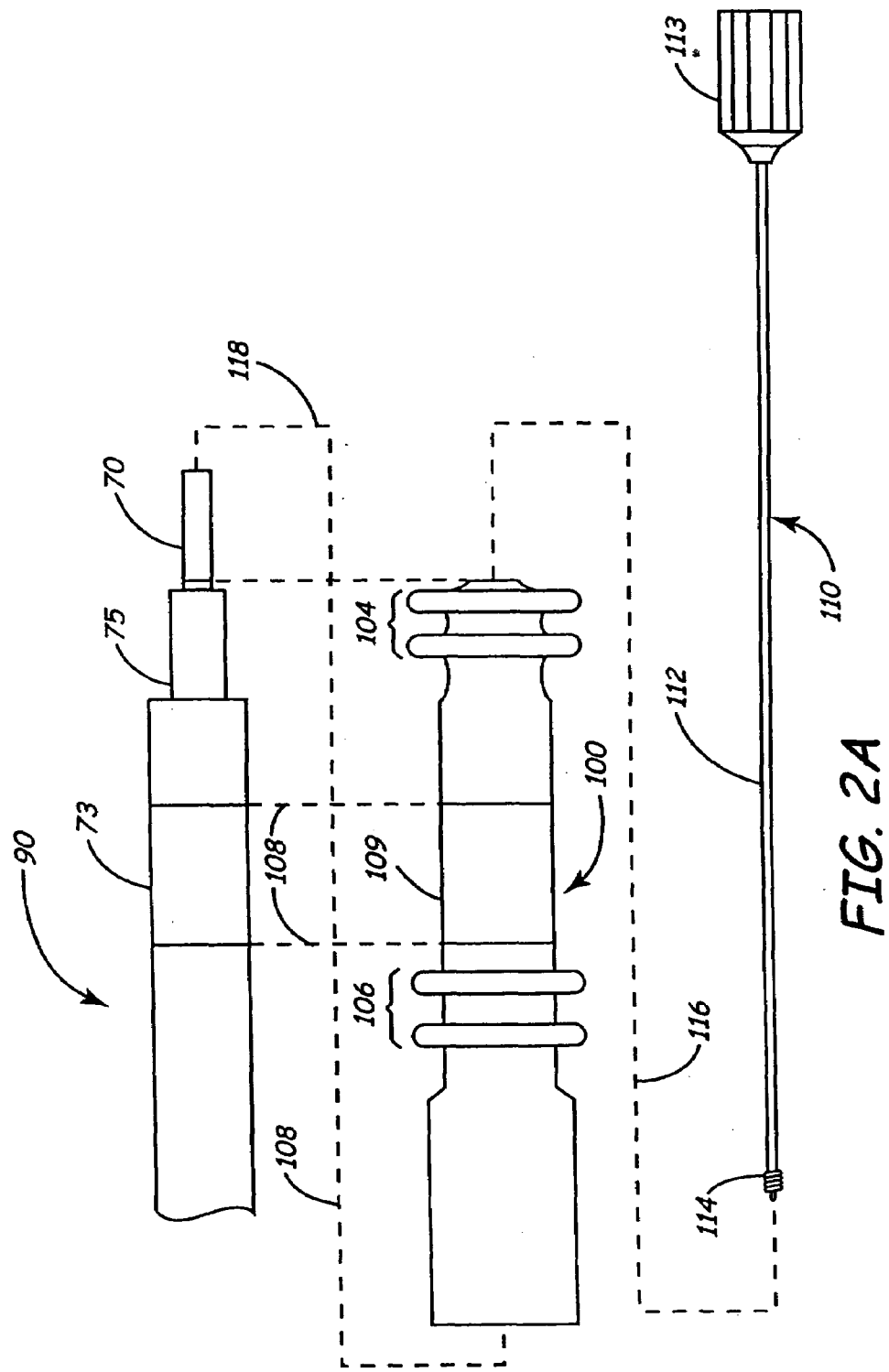

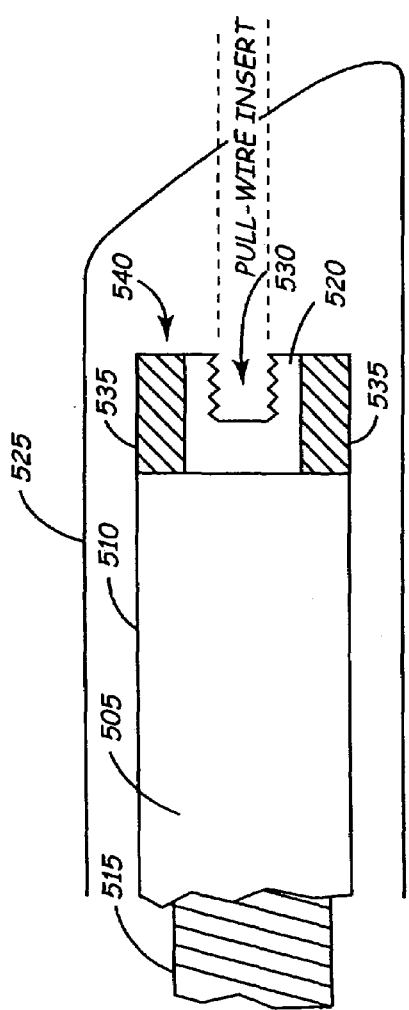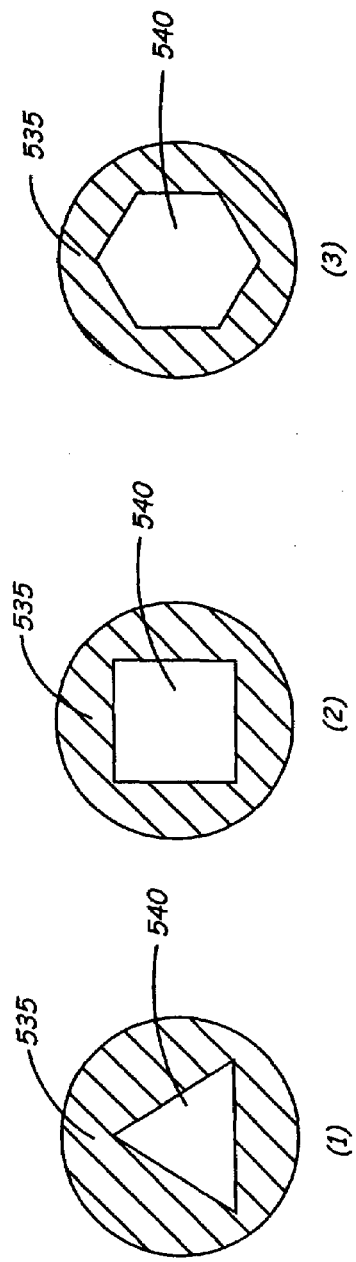
FIG. 11D
FIG. 11E

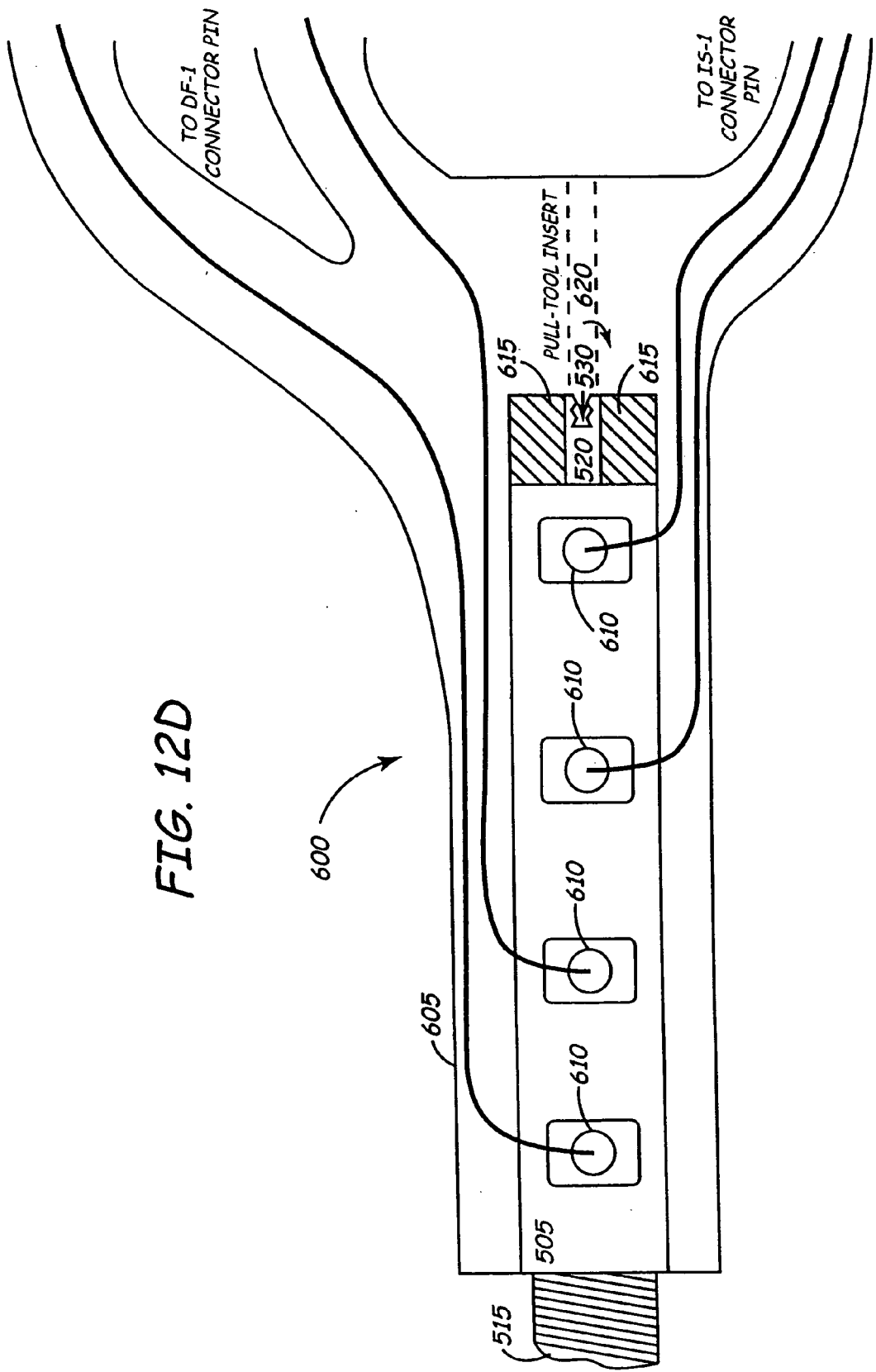

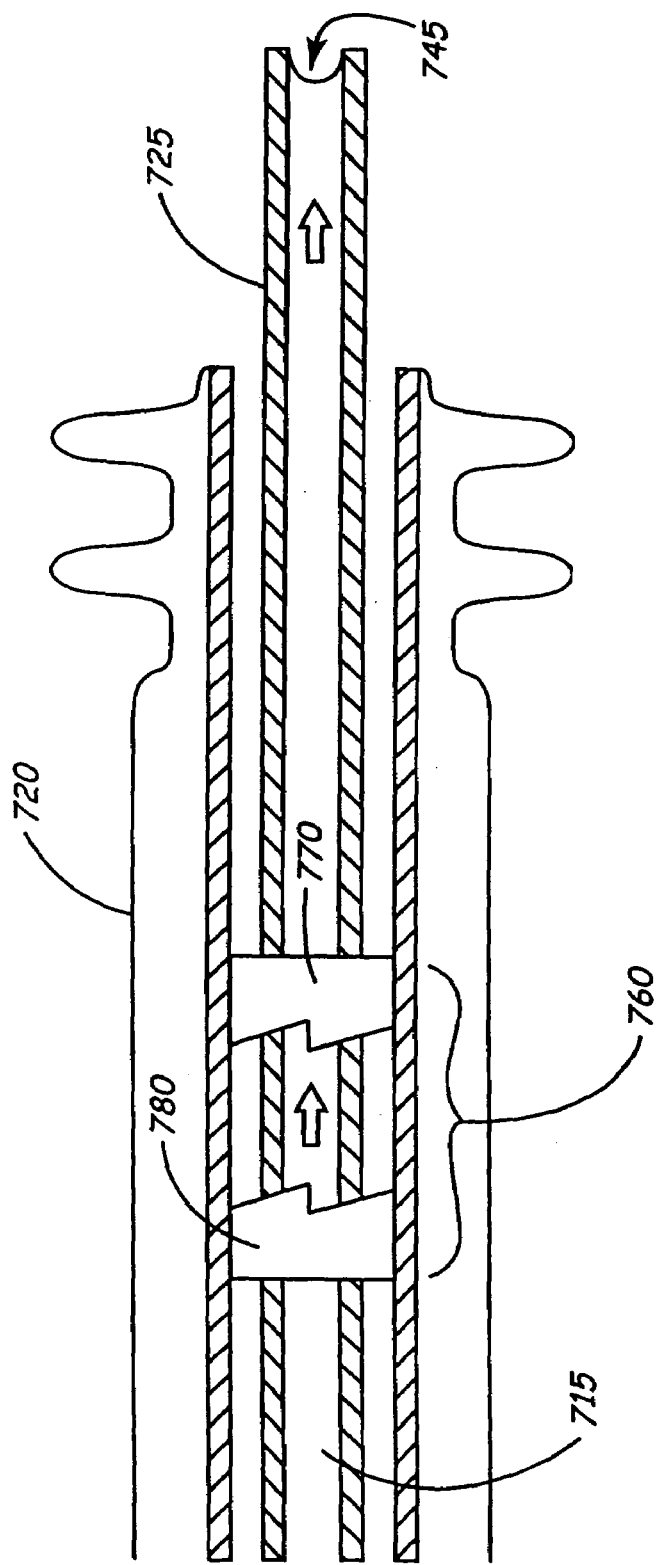

MEDICAL LEAD AND LEAD CONNECTOR SYSTEM

PRIORITY CLAIM

This Application is a divisional of U.S. application Ser. No. 10/040,143, filed Jan. 3, 2002, now U.S. Pat. No. 6,854,994, entitled "Medical Lead and Lead Connector System," which is a continuation-in-part of U.S. application Ser. No. 09/838,814, filed Apr. 19, 2001, now U.S. Pat No. 6,705,900, entitled "Lead Up-Sizing Sleeve," which claims priority from provisional U.S. application Ser. No. 60/270,074, filed Feb. 21, 2001.

BACKGROUND OF THE INVENTION

The present invention relates generally to mechanisms for interconnecting electrical leads and electrical medical devices; and more particularly, to systems and methods of interconnecting implantable electrical leads and implantable medical electrical devices such as pacemakers, nerve stimulators, implantable defibrillators, implantable monitors, and so forth.

DESCRIPTION OF THE RELATED ART

As implantable electrical devices have increased in their complexity, there has been an increasing variety of electrical lead systems developed for use in conjunction with these devices. Nowhere is this more apparent than in the context of implantable cardioverter/defibrillators, which may include three, four, five, or more electrodes located on various numbers of implantable electrical leads. The leads themselves may carry one, two, three, or more electrodes, and may employ a variety of different electrical connector configurations and types. As a result, manufacturers of implantable cardioverter/defibrillators have had to produce their products with a variety of connector block configurations, capable of use with different lead systems. For example, Medtronic, Inc. presently manufactures implantable cardioverter/defibrillators with four basic connector designs, designated configurations "B", "C", "D", and "E". The "B" configuration includes three 6.5 mm connector bores for receiving high voltage electrical lead connectors of the type used to couple to cardioversion/defibrillator electrodes and one 3.2 mm in-line electrical connector bore compatible with the IS-1 connector standard for receiving an IS-1 electrical lead connector of the type generally used to couple to cardiac pacing and sensing electrodes. The "C" configuration includes a single 3.2 mm connector bore conforming to the DF-1 standard for receiving high voltage electrical lead connectors used to couple to cardioversion/defibrillation electrodes. This configuration also includes a single IS-1 connector bore. The "D" configuration includes three DF-1 connector bores and one IS-1 connector bore. The "E" configuration includes two 6.5 mm connector bores and two 5 mm connector bores for receiving electrical lead connectors used to couple to individual cardiac pacing and sensing electrodes.

As is apparent from the above discussion, multiple connectors block types are necessitated both by the use of multiple connector standards, and also because of the desire to connect a varying number of lead systems to a given device. The situation is complicated even further by the use of non-standard connector systems. For example, it has been increasingly common to utilize small-diameter guide catheters to deliver leads having a diameter of 7 French or less to a desired implant site. After lead placement is completed, the catheter must be withdrawn from the body. However, if the catheter has a small inner diameter, the inner lumen of the catheter cannot accommodate a standard-size lead connector such as one conforming to the IS-1 standard. In this situation, the catheter must be split or slit into two portions. Such slittable or splittable catheters are more expensive to manufacture, and require the additional slitting step to remove. To remedy this problem, the lead may instead include a small-diameter, non-standard connector that easily fits within the catheter lumen, allowing the catheter to be readily withdrawn from the body. This non-standard connector has the drawback of necessitating the use of an even larger number of connector block configurations.

One way to solve the problem is to provide adapters that adapt one lead connector type to a different connector type on the device. These adapters may take the form of a relatively short lead, which at one end has a connector assembly that may be inserted into one or more bores on the connector block on the implantable device and at the other end has one or more connector bores capable of receiving the connector assembly or assemblies on the electrical leads to be used with the device. These adapters are bulky and add substantially to the size of the pocket in which the device is to be implanted. In addition, they tend to require a number of additional steps to be performed by the physician in order to couple the leads to the implanted device, and are thus seen as generally undesirable. Such adapters are disclosed in U.S. Pat. No. 5,000,177, issued to Hoffmann, and U.S. Pat. No. 5,328,442, issued to Levine. Some adapters, such as disclosed in U.S. Pat. No. 5,050,602 issued to Osypka and U.S. Pat. No. 5,060,649 issued to Hocherl et al. even required removal of the connector assembly of the lead as part of the connection process.

Another approach to resolving lead/device incompatibility problems involves use of an up-sizing adapter. An up-sizing adapter is used to convert a smaller-diameter standard or non-standard lead connector to a larger-sized device connector. This is particularly useful when dealing with leads having smaller connectors for use with non-splittable guide catheters. As discussed above, a smaller lead connector allows guide catheters to be easily withdrawn over the lead proximal end after the implant procedure is completed. After the guide catheter has been removed from the body, the up-sizing adapter may be connected to allow the lead to be coupled to a device.

One example of an up-sizing adapter is shown in U.S. Pat. No. 5,007,864, issued to Stutz Jr. This patent discloses an adapter to convert a smaller-diameter bipolar lead system to a larger connector block. Although this system allows a small-diameter lead to be used with a non-splittable catheter, this system has a disadvantage of not being adaptable for use with bipolar leads.

Another example of an up-sizing adapter is disclosed in U.S. Pat. No. 4,583,543 issued to Peers-Trevarton. While this system is adaptable for use with bi-polar lead systems, it can only be used with a lead having a connector pin that is smaller than the connector bore. That is, it is not adaptable for use with a lead having a standard connector pin size but a non-standard connector body.

What is needed, therefore, is an improved system and method for allowing a lead connector of a first size to couple to a larger-sized device connector, and that addresses the foregoing problems.

In addition to the aforementioned problems, the connector pin and lead are typically fed through the connecting adapter using a pull-wire device that is screwed into a threaded recess of the connector pin's tip. After the connector pin is pulled into the connector (axial) bore of the connecting adapter, the pull-wire device is unscrewed from the threaded recess of the connector pin's tip. Typically, the unscrewing of the pull-wire device may cause the connector pin to axially rotate within the connector bore, and, consequently, may provide enough torque on the lead to cause the implanted electrodes to become dislodged from the patient's internal organs. As a result of such axial rotation of the lead, and subsequent dislodging of the electrode, the implantation process of the lead and electrode would have to be performed again, thus resulting in additional time, costs, and/or trauma to the patient. The present invention is directed to overcoming or at least reducing the effects of one or more problems set forth above.

SUMMARY OF THE INVENTION

In one aspect of the present invention, a lead connector arrangement is provided. The lead connector arrangement includes a non-cylindrically shaped connector pin coupled to a lead conductor. A connector sleeve assembly receives the non-cylindrically shaped connector pin, and includes an insert with an axial bore formed therein that complements the shape of the connector pin.

In another aspect of the present invention, a method is provided. The method includes providing a non-cylindrically shaped connector pin coupled to a lead conductor. A connector sleeve assembly is provided to receive the non-cylindrically shaped connector pin, where the connector sleeve assembly includes an insert with an axial bore formed therein that complements the shape of the connector pin. The non-cylindrically shaped connector pin is then inserted within the axial bore of the insert.

In another aspect of the present invention, a lead connector arrangement is provided. The arrangement comprises a non-cylindrically shaped connector pin coupled to a lead conductor. An adapter block assembly receives the connector pin within a cavity formed therein, and is capable of connecting the lead conductor to at least two types of connector standards. The adapter block assembly includes an insert with an axial bore formed therein within the cavity that complements the shape of the connector pin.

In another aspect of the present invention, a method is provided. The method includes providing a non-cylindrically shaped connector pin coupled to a lead conductor. An adapter block assembly is provided to receive the connector pin within a cavity formed therein. The adapter block assembly is capable of connecting the lead conductor to at least two types of connector standards. The adapter block assembly includes an insert with an axial bore formed therein within the cavity that complements the shape of the connector pin. The connector pin is inserted within the axial bore of the insert.

In another aspect of the present invention, a lead connector arrangement is provided. The arrangement comprises a connector pin coupled to a lead conductor. A connector sleeve assembly having a cavity formed therein receives the connector pin and lead conductor. The arrangement further comprises a retraction stop mechanism to reduce axial rotation of the lead conductor within the connector sleeve assembly when the connector pin is fully extended within the connector sleeve assembly.

In another aspect of the present invention, a method to reduce axial rotation of a lead conductor within a connector sleeve assembly is provided. The lead conductor has a connector pin affixed to one end thereof. A threaded pull tool is screwed into an inner threaded recess within a tip of the connector pin. The lead conductor is pulled within a cavity of the connector sleeve assembly until a movable retraction stop member of the lead conductor engages with a fixed retraction stop member of the connector sleeve assembly. The threaded pull tool is unscrewed from the inner threaded recess of the connector pin during the engagement of the moveable and fixed retraction stop members.

BRIEF DESCRIPTION OF THE DRAWINGS

The invention may be understood by reference to the following description taken in conjunction with the accompanying drawings, in which like reference numerals identify like elements, and in which:

FIG. 2A is a plan view of one embodiment of an upsizing sleeve according to the current invention;

FIG. 11D is a side view perspective of the connector sleeve assembly with a non-cylindrically shaped connector pin fully inserted therein;

FIG. 11E is a front view perspective of a molded form insert, with an axial bore formed therein, within the connector sleeve assembly;

FIG. 12D is a side view perspective of a trifurcated adapter block assembly with the non-cylindrical connector pin fully inserted therein according to another embodiment;

FIG. 13B is a side view perspective of a connector sleeve assembly of the lead connector arrangement of FIG. 13A.

Figure 1A:
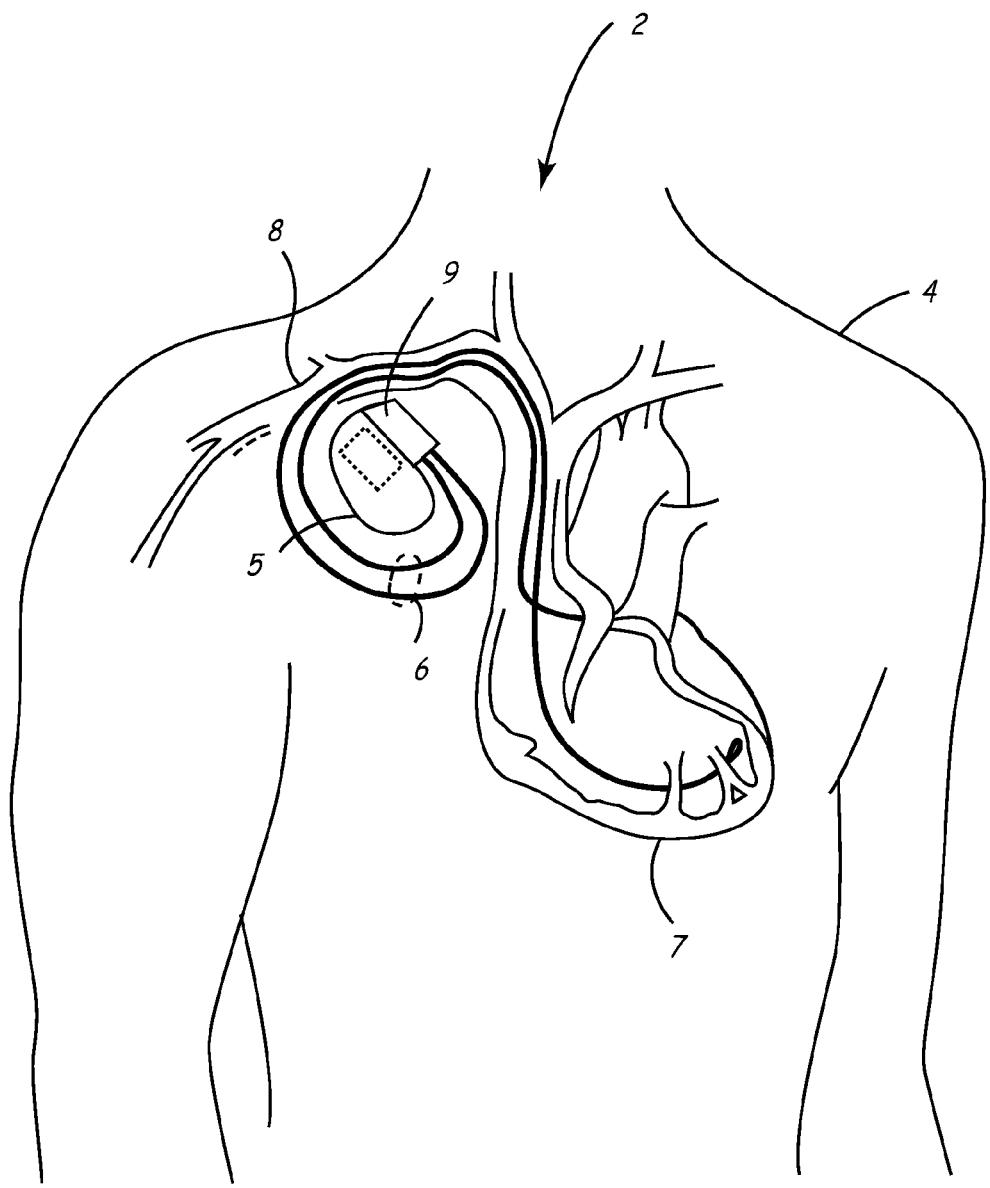
FIG. 1A schematically illustrates one embodiment of an implantable medical device in the form of a pacemaker and associated leads positioned to stimulate and/or sense the heart.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the spirit and scope of the invention as defined by the appended claims.

DETAILED DESCRIPTION OF SPECIFIC EMBODIMENTS

Turning now to the drawings, and specifically referring to FIG. 1A, an implantable medical device (IMD) system 2 that includes an implantable medical device 5 is provided. In accordance with one embodiment, the implantable medical device 5 may take the form of a pacemaker, cardioverter, defibrillator, neural stimulator, or drug administering device that has been implanted within a patient's body 4. It will be appreciated that the implantable medical device 5 may take the form of various other medical devices, and, thus, need not necessarily be limited to the aforementioned examples.

The implantable device 5 is housed within a hermetically sealed, biologically inert outer container or housing, which may itself be conductive so as to serve as an electrode in the pacemaker's pacing/sensing circuit. One or more pacemaker leads, collectively identified with reference numeral 6 in FIG. 1A, are electrically coupled to the implantable device 5 and extend into the patient's heart 7 via a vein 8. In accordance with the illustrated embodiment, the leads 6 are coupled to the implantable device 5 via an up-sizing or connector sleeve assembly 9. Disposed generally near a distal end of the leads 6 are one or more exposed conductive electrodes for sensing cardiac activity, delivering electrical pacing stimuli to the heart 7, or providing a stimulating voltage to defibrillate the heart 7. The leads 6 may be implanted with their distal end situated adjacent the atrium or the ventricle, or both, of the heart 7.

Figure 1B:
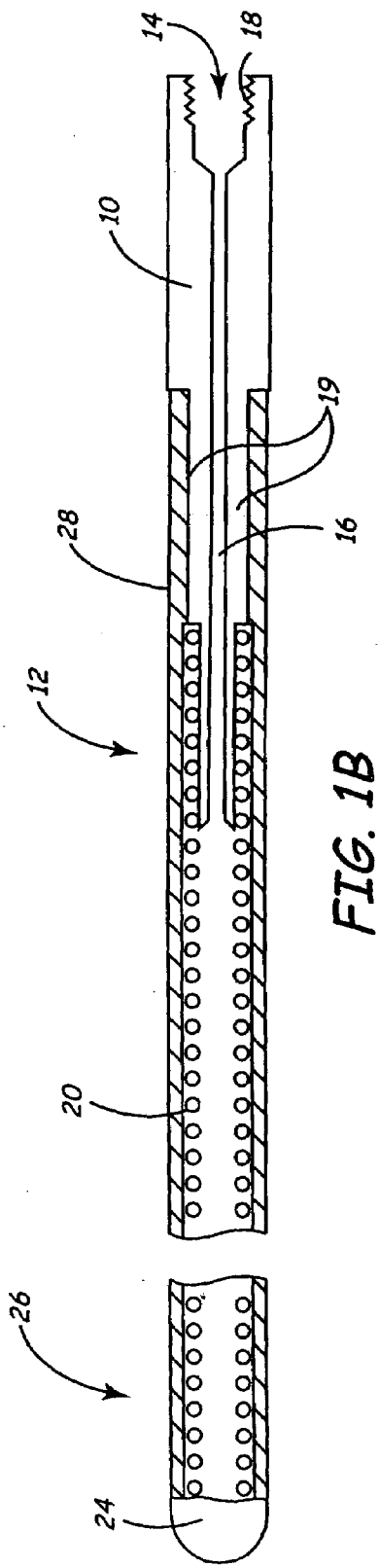
FIG. 1B is a side cutaway view of an exemplary unipolar lead connector of the type that may be employed with the current inventive system.

FIG. 1B is a side cutaway view of an exemplary unipolar lead connector of the type that may be employed with the current inventive system. The lead includes a connector pin 10 at the proximal end of the lead. In this view, the connector pin 10 has substantially the same diameter as the lead body 12, although this is not necessary. Connector pin 10 has an opening 14 that extends to inner lumen 16. A portion 18 of inner lumen 16 may be threaded.

Connector pin 10 couples to conductive member 19 that extends into lumen 16 and is electrically and mechanically coupled to at least one conductor 20. In FIG. 1B, conductor 20 is a conductive coil that extends the length of the lead body 12 to a tip electrode 24 at the lead body distal tip 26. In other embodiments, conductor 20 may take the form of a single-filar or multi-filar stranded conductor.

Lead body further includes an insulative jacket 28 that may be formed of a biocompatible polymer such as polyurethane or silicone. It may be noted that the lead of FIG. 1B is merely exemplary, and many other leads may be employed with the current invention. For example, a lead without an inner lumen extending within lead body 12 may be utilized. Alternatively, a lead having multiple inner lumens may likewise be utilized.

Figure 1C:
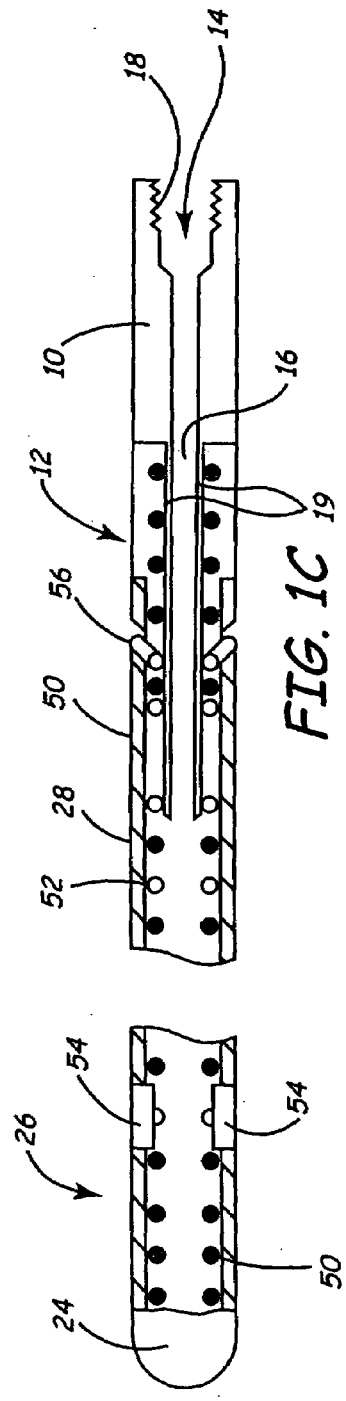
FIG. 1C is a side cutaway view of an exemplary bipolar lead connector of the type that may be employed with the current inventive system.

FIG. 1C is a side cutaway view of an exemplary bipolar lead connector of the type that may be employed with the current inventive system. The lead of FIG. 1C includes a connector pin 10 that couples to conductive member 19. Conductive member 19 is electrically and mechanically coupled to an insulated coiled conductor 50. This conductor 50 extends the length of lead body 12 and is coupled at the distal tip 26 to tip electrode 24. A second insulated coiled conductor 52 is also provided to couple to ring electrode 54 at the lead distal end to ring connector 56. In another embodiment, the conductors may be single or multi-filar stranded conductors.

Figure 1D:
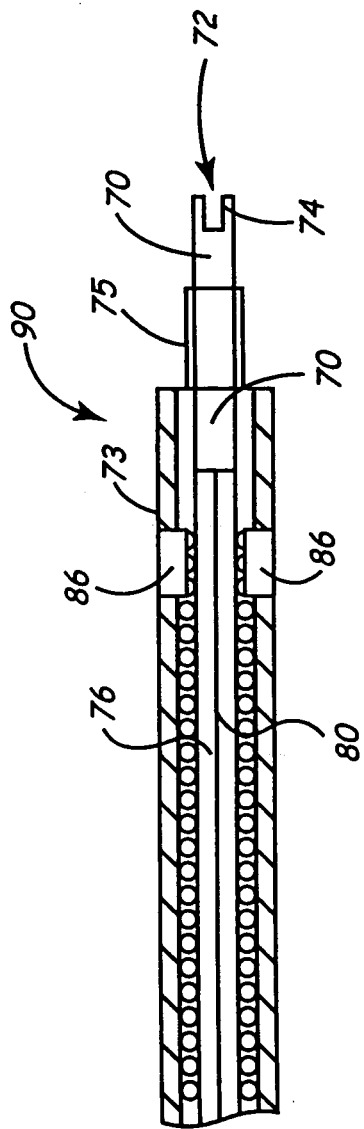
FIG. 1D is a side cutaway view of yet another exemplary bipolar lead connector of the type that may be employed with the current inventive system.
Figure 1D:
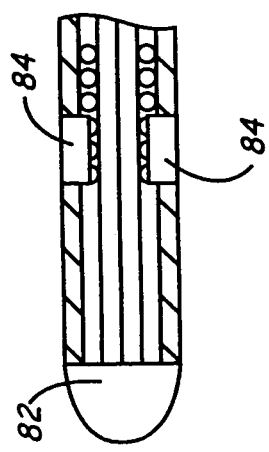

FIG. 1D is a side cutaway view of yet another exemplary bipolar lead connector of the type that may be employed with the current inventive system. In this embodiment, a connector pin 70 is shown having an opening 72 that includes an inner, threaded surface 74. A portion of the connector pin is shown surrounded by an insulative sleeve 75, which may be formed of a polymer. This insulative sleeve electrically isolates pin from lead body 73, and provides additional structural support. The connector pin, which may have dimensions conforming to an IS-1 or another standard, extends within an inner lumen 76 of the lead body 73. This inner lumen houses a stranded conductor 80 such as shown in commonly-assigned U.S. Pat. No. 5,760,341 that is electrically coupled to tip electrode 82. The conductor 80 may be a single or multi-filar stranded conductor, or in a different embodiment, may be a coiled conductor. A second, coiled conductor 84 electrically couples ring electrode 86 to a connector ring 88. It may be noted that although the connector pin 70 of this design may be of a dimension that corresponds to a standard such as an IS-1 connector pin standard, the overall lead dimensions of the proximal end 90 of the lead do not necessarily conform to any standard.

As discussed above, the lead configurations shown in FIGS. 1B, 1C, and 1D have small connector profiles. Therefore, a guide catheter used to place the leads during an implant procedure may be readily withdrawn over the connector pin without having to split or slit the catheter body. However, the connector pin 10 and the proximal end 11 of the lead body do not conform to a connector standard such as IS-1, making connection to a standard device connector block difficult. The upsizing sleeve of the current invention is provided as a means for facilitating this connection so that a specialized device connector block is not needed.

FIG. 2A is a plan view of one embodiment of an upsizing sleeve 100 according to the current invention. This upsizing sleeve is a generally tubular member having an inner lumen (not shown in FIG. 2) that is adapted to receive the proximal end of a lead such as the lead shown in FIG. 1D. The inner lumen of the upsizing sleeve is slightly larger than the outer diameter of proximal end 90 of the lead. For example, the proximal end 90 of the lead of FIG. 1D may be adapted to fit within the inner lumen as indicated by dashed line 102 such that the lead body forms a press fit with the surface defined by the lumen. The upsizing sleeve is adapted to conform to a standard configuration such as an IS-1 standard.

Upsizing sleeve is shown to include two sets of exterior sealing rings 104 and 106 adapted to sealingly engage with the connector port of a device such as a pacemaker or defibrillator. Upsizing sleeve further includes a conductive ring member 109 adapted to electrically couple to connector ring 73 of the lead, as shown by dashed lines 108 in a manner to be discussed further below. Conductive ring member 109 is further adapted to mechanically and electrically couple to a set screw within the device connector to thereby couple ring connector 73 to a medical device in a manner dictated by the IS-1 connector standard. Sealing rings and the portions of upsizing sleeves surrounding conductive ring member 109 may be formed of one or more polymer structures such as polyurethane or silicone in a manner to be discussed further below.

Because of the relatively tight press-fit between the proximal end 90 of the lead and the upsizing sleeve 100, a pull-wire device 110 may be provided to aid in the insertion process. One embodiment of the pull-wire device 110 includes a rigid pull-wire 112 and a handle 113. The rigid pull-wire 112 may include a threaded distal end 114, which is inserted through the inner lumen of upsizing sleeve 100, as shown by dashed line 116. The threads of threaded distal end 114 are then positioned to engage threaded surface 74 (FIG. 1D) of the connector pin 70, as shown by dashed line 118. This allows the pull-wire 112 to rigidly engage the proximal end 90 of the lead so that the lead may be pulled through the inner lumen of the upsizing sleeve 100.

Although FIG. 2A shows pull-wire 112 including threaded distal end 114 to engage a lead, other coupling means could be provided to be coupled to the lead, including a spring-loaded clip, or a plug to form a press-fit with opening 72.

Figure 2B:
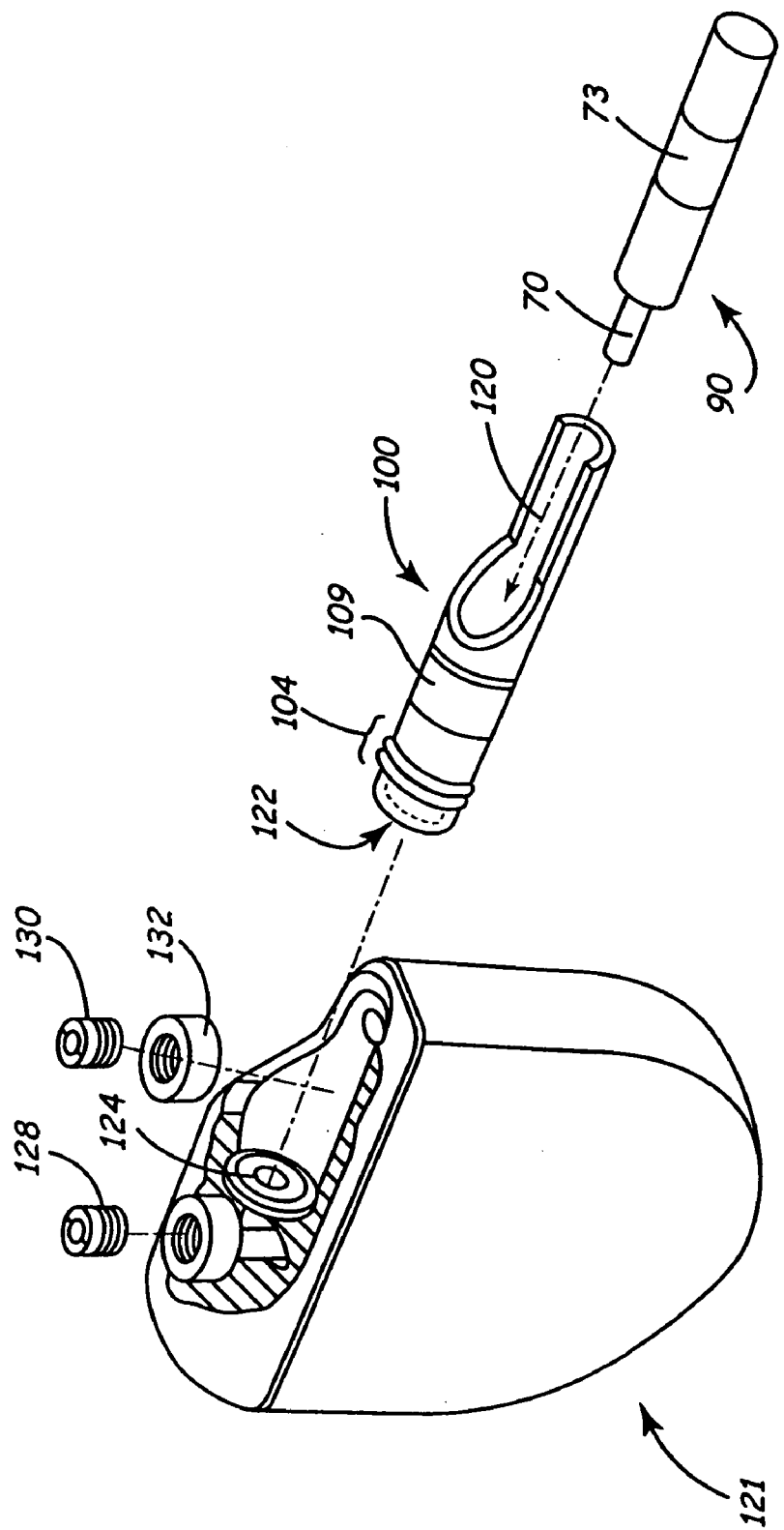
FIG. 2B is a perspective view illustrating the manner in which the inventive up-20 sizing sleeve may be used to couple a lead to a medical device.

FIG. 2B is a perspective view illustrating the manner in which the inventive up-sizing sleeve may be used to couple a lead to a medical device. The proximal end 90 of a lead such as shown in FIG. 1C includes a connector pin 70 and connector ring 73. This lead may be inserted into the inner lumen 120 of sleeve 100 so that connector ring 73 forms a press fit with conductive ring member 109, with connector pin 70 extending through the proximal end 122 of the sleeve. Connector pin is adapted to be received by port 124 of the medical device 126, which is further maintained by set-screw 128. A second set-screw 130 and washer 132 is provided to form a connection with conductive ring member 109.

Figure 3:
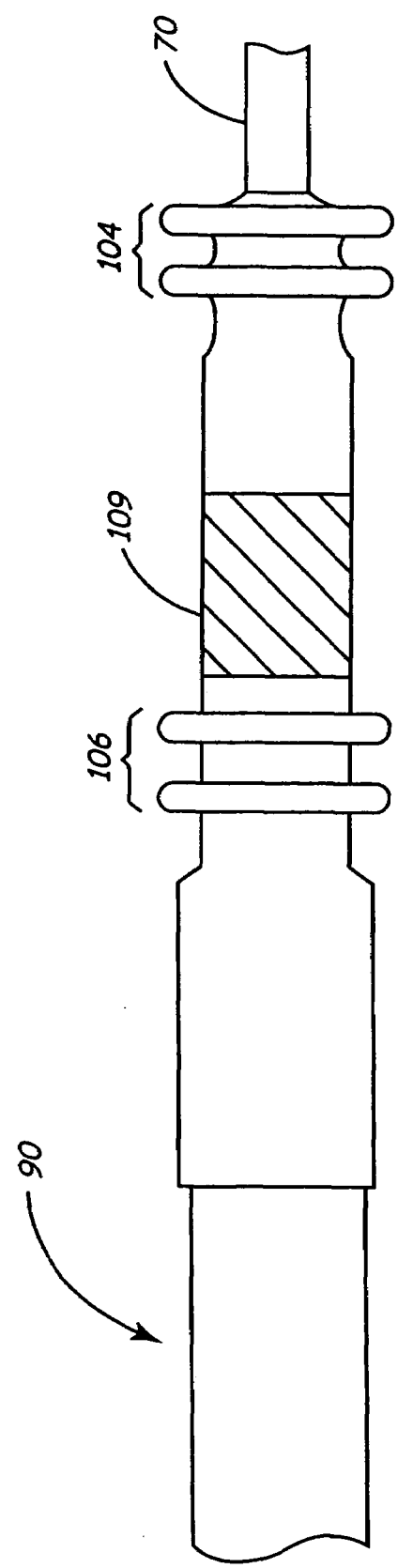
FIG. 3 is a plan view illustrating proximal end of the lead of FIG. 1C inserted within upsizing sleeve.

FIG. 3 is a plan view illustrating proximal end 90 of the lead of FIG. 1D inserted within upsizing sleeve 100. Connector pin 70 extends through the proximal end of the upsizing sleeve, whereas the lead body of proximal end extends out the distal end of the upsizing sleeve.

Figure 4A:
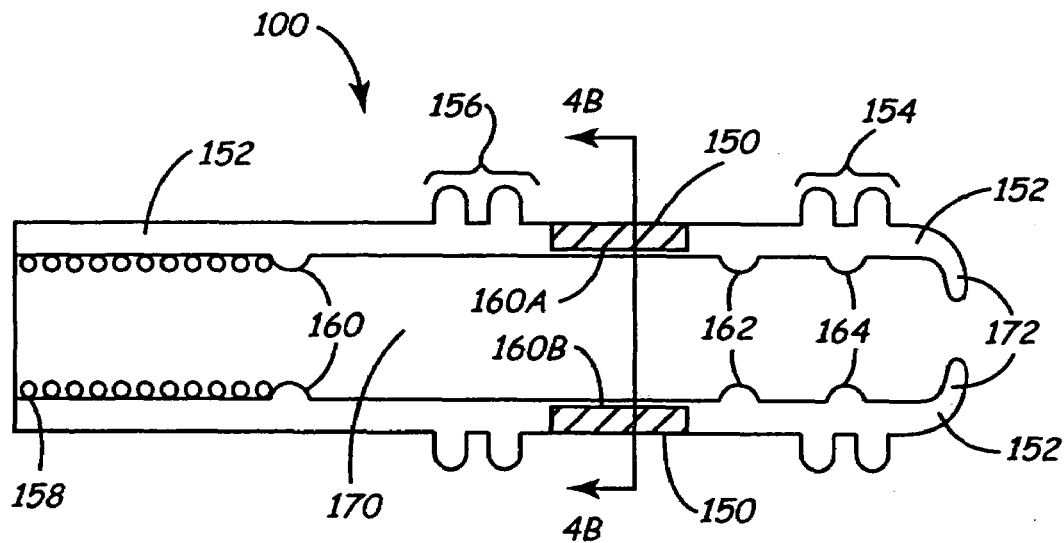
FIG. 4A is a side cutaway view of one embodiment of the upsizing sleeve of the current invention that may be formed using an over-molding process.

FIG. 4A is a side cutaway view of one embodiment of upsizing sleeve 100. A conductive ring member 150 is provided to couple to a connector ring such as connector ring 73 (FIG. 1D) of a lead in the manner discussed above. This ring member may be formed of any conductive material such as stainless steel, for example. The remainder of the upsizing sleeve is an integral structure 152 that includes sealing rings 154 and 156. This structure may be formed of a biocompatible polymer such as silicone using a silicone over-molding process as is known in the art. According to one aspect of the invention, the upsizing sleeve may be reinforced at the distal end with a reinforcing member 158 that may be formed of an insulative coil such as a PTFE coil, a conductor coil that may or may not be insulated, or any other material having strength properties that make it suitable for this purpose. This reinforcing member provides added support to prevent the lead proximal end 90 (FIG. 3) from flexing in a manner that may cause lead failures over time. In another embodiment, a reinforcing, tubular sleeve member may be inserted within the distal end of the upsizing sleeve to provide this type of support.

Upsizing sleeve may further include interior sealing rings within the inner lumen 170. For example, upsizing sleeve of FIG. 4A includes sealing rings 160, 162 and 164 to provide a fluid-tight seal with a lead inserted within inner lumen 170. Finally, upsizing sleeve is also shown to have a lip 172 at the proximal end, which may be provided to engage a corresponding structure on the lead. In this manner, upsizing sleeve is positioned over the lead so that connector pin 70 extends beyond the proximal end of upsizing sleeve 100 a predetermined distance that conforms to a given connector standard. For example, lip 172 may be adapted to engage the ridge formed by insulative sleeve 175 where the insulative sleeve meets the connector 70 (FIG. 1D).

Figure 4B:
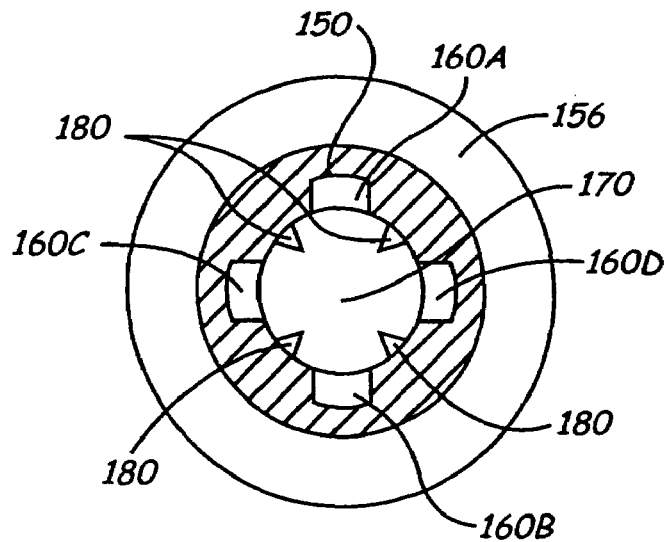
FIG. 4B is a cross-sectional view of upsizing sleeve at line 4B-4B of FIG. 4A.

FIG. 4B is a cross-sectional view of upsizing sleeve at line 4B-4B of FIG. 4A. This view shows conductive ring member 150 including channels adapted to receive a polymer during an over-molding process such as a silicon over-molding process discussed above. The flow of a polymer into these channels results in the formation of the connecting polymer structures 160A, 160B, 160C, and 160D. FIG. 4B further illustrates conductive teeth members 180 coupled to, or integrally formed, in conductive ring member 150. These conductive teeth members are adapted to engage a conductive ring of a lead such as connector ring 73 to form a more robust electrical connection between the connector ring and conductive ring member 150. This view further illustrates sealing rings 156.

Although teeth members 180 are shown in FIG. 4B to couple conductive ring member to a connector ring of a lead, many other mechanisms may be used in the alternative. For example, a keyed mechanism such as a woodruff or spline key may be used to lock a lead ring connector to the conductive ring member. Alternatively, a threaded aperture may be provided in the connective ring member so that a set-screw from a device connector block may be used to affix the sleeve to the lead via the threaded aperture. In yet another embodiment, small ports may be provided in the conductive ring member to receive conductive adhesive to enhance the electrical and mechanical contact between the conductive ring member and the lead ring connector. Alternatively, a hole in the conductive ring member may be aligned with a corresponding hole or groove in the lead so that a pin or rivet can be inserted to form a mechanical and electrical coupling. A thumb-actuated spring and ball-detent mechanism could be used to couple the sleeve to the lead. Another embodiment may include a thumb-activated push-collar such as is provided on steerable stylet handles. Any other type of coupling mechanisms may be used to form a stable electrical and mechanical fit between the conductive ring member and the connector ring of a lead.

Figure 5:
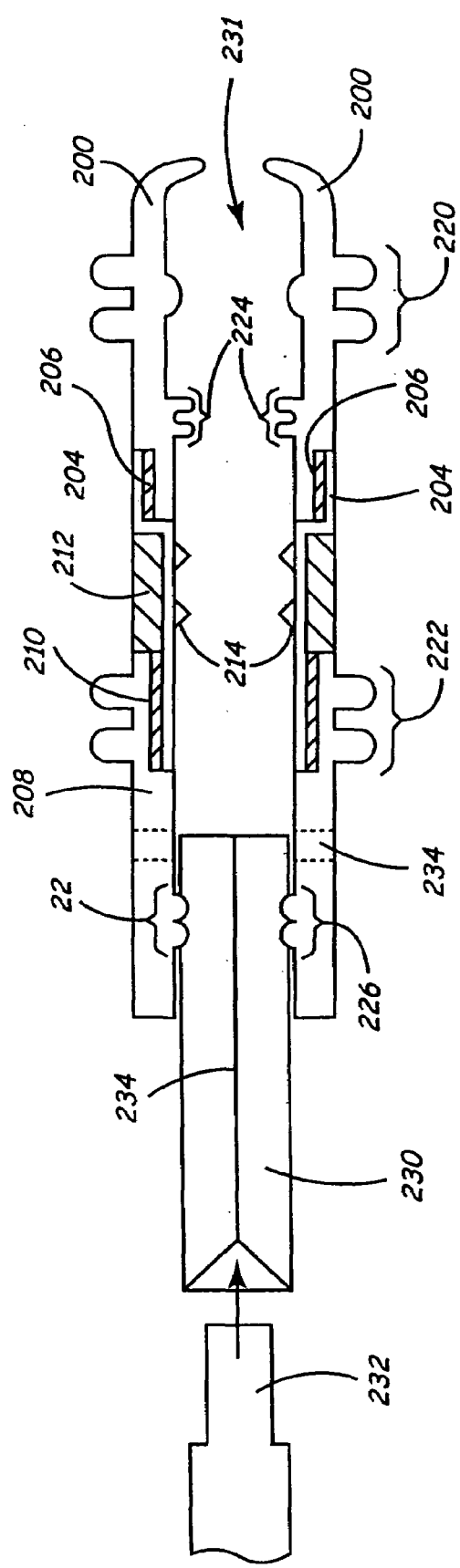
FIG. 5 is a cutaway side view of another embodiment of the upsizing sleeve of the current invention.

FIG. 5 is a cutaway side view of another embodiment of the upsizing sleeve of the current invention. In this embodiment, a first generally tubular member 200, which may be formed of silicone, is bonded to a support member 204 using a first layer 206 of medical-grade adhesive. Support member, which may be formed of a material that is more rigid than the silicone such as a higher durometer polyurethane, is also bonded via adhesive layer 210 to a second generally tubular member 208, which may also be silicone. The support member 204 is adapted to provide additional structural rigidity that is not provided by a sleeve formed entirely of a lower-durometer material such as silicon. This rigidity is important to maintain precise sleeve dimensions so that the sleeve maintains a form that conforms to a predetermined standard even after undergoing the strain of forming a press fit with a lead.

A conductive ring member 212 surrounds the support member 204 and is adapted to engage a set-screw of a medical device as is provided on a standard IS-1 device connector block. In one embodiment, the conductive ring member 212 includes teeth 214 that extend through the support member to engage a connector ring of a bipolar lead. If a unipolar lead is to be employed, these teeth need not be included in the sleeve, since the ring connector of the lead need not make an electrical connection with a device connector block.

Each of tubular members 200 and 208 includes exterior sealing rings 220 and 222, respectively, to provide a fluid-tight seal with a device connector block. Each of the tubular members further includes interior sealing rings 224 and 226, respectively, to provide the fluid tight seal with a lead. As discussed above, preferably tubular members 200 and 208 are formed of a less rigid material such as silicone so that these sealing rings are more deformable and better able to provide a seal.

FIG. 5 also illustrates an alternative mechanism that may be used to engage a lead with the sleeve. A split tubular member composed of a material having a lubricious surface such as PTFE tubing 230 may be inserted in the distal end of the sleeve. The lubricious outer surface of the tubing allows the tubing 230 to be readily inserted into inner lumen 231 of the sleeve. A lead 232 may then be inserted within the inner lumen of the tubing 230 and the tubing removed. The slit 234 in the tubing allows it to be removed from around the lead after the lead is attached to the up-sizing sleeve. The use of this split tubular member thereby provides an alternative to the pull-wire tool (FIG. 2) as an aid in forming the press fit between a lead and the sleeve.

In one embodiment, sleeve may include one or more ports such as port 234 (shown dashed) to allow a medical-grade adhesive to be infused or injected between the sleeve and the lead after the lead is inserted into the sleeve to thereby secure the lead to the sleeve.

Figure 6:
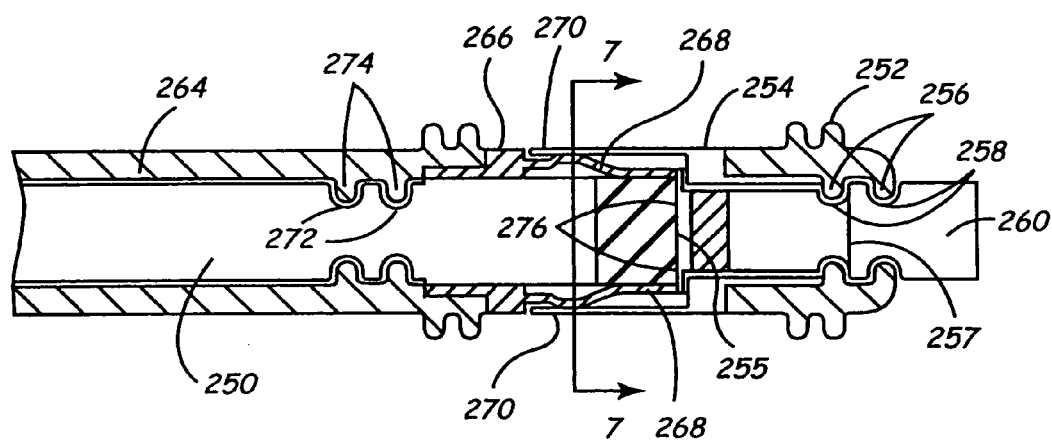
FIG. 6 is a cutaway side view of a two-piece sleeve member that may be assembled over the lead at the time of use.

FIG. 6 is a cutaway side view of a two-piece sleeve member that may be assembled over a lead such as lead 250 at the time of use. A first portion of the sleeve includes a less rigid, generally tubular member 252 that may be formed of a silicon, and which is bonded to a conductive ring 254 via a medical-grade adhesive. Conductive ring 254, which is formed of a conductive material, is adapted to electrically and mechanically couple to a connector ring 255 of lead 250 via a second portion of the sleeve, as will be discussed further below. Conductive ring is further adapted to electrically couple to a connector block of a medical device, as may be accomplished using a set.-screw.

In one embodiment, the tubular member 252 includes one or more lips 256 to engage grooved members 258 in the lead connector pin 260. This allows the sleeve to be seated over the lead so that the dimensions of the assembly conform to a predetermined standard such as IS-1. Lips 256 further provide a fluid-tight seal with lead 250. One of the lips 256 is shown interfacing with a seal zone 257 of the inline connector. As discussed above, tubular member 252 may be formed of a less rigid material such as silicone to provide sealing rings that allow for a better fluid-tight seal.

The two-piece sleeve of FIG. 6 further includes a second portion that is formed of a second less-rigid tubular member 264 such as silicone. Tubular member 264 is bonded to a connector member 266, which may be formed of a metal. Connector member 266 has deformable fingers 268 that slide under edge 270 to engage conductive ring 254 in a snap-fit that provides both a mechanical and electrical coupling between connector member 266 and conductive ring 254. Deformable fingers 268 also electrically couple to connector ring 255 of lead 250 so that an electrical connection is formed between the connector ring 255 and conductive ring 254 of the two-piece sleeve. This allows the connector ring 255 of lead 250 to be coupled to a connector block of a device via conductive ring 254.

The lead 250 of FIG. 6 may include grooves 272 to engage inner sealing rings 274, and may further having a shoulder 276 to engage conductive ring 254 in a manner that further allows the lead to seat in a position that conforms to a predetermined standard.

Figure 7:
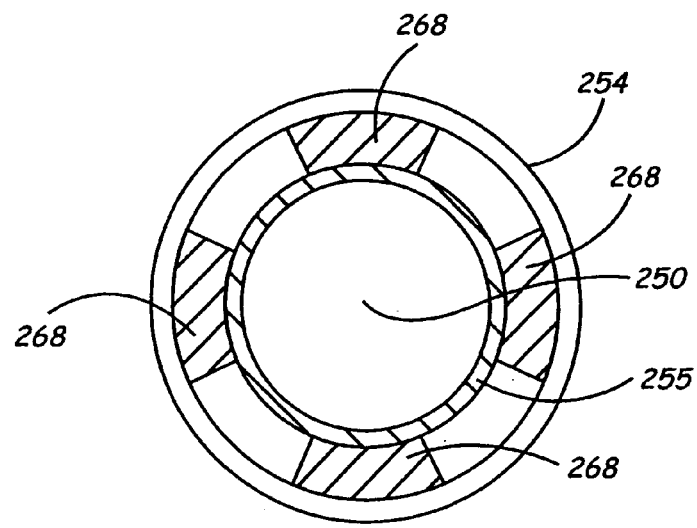
FIG. 7 is a cross-sectional view of the sleeve of FIG. 6 at line 7-7.

FIG. 7 is a cross-sectional view of the sleeve of FIG. 6 at line 7-7. This view shows the deformable fingers 268 electrically and mechanically engaging conductive ring 254, and further electrically engaging connector ring 255 of lead 250.

Figure 8:
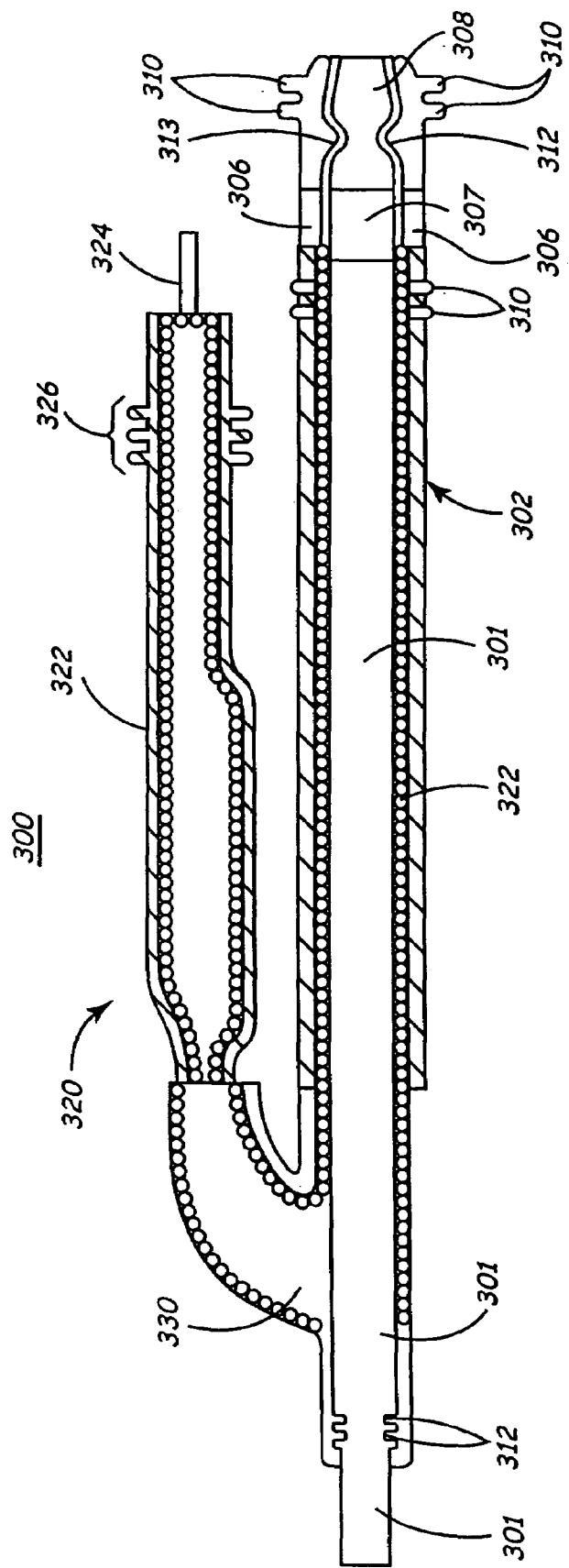
FIG. 8 is a cutaway side view of a bifurcated sleeve that includes two different connector standards.

FIG. 8 is a cutaway side view of a bifurcated sleeve 300 designed to adapt a lead to conform to two different connector standards. In the embodiment illustrated, lead 301 is shown engaging a first bifurcation 302 of the bifurcated sleeve that conforms to the IS-1 standard. This portion of the sleeve may be of any of the embodiments discussed above. A conductive ring member 306 is provided on bifurcation 302 to engage with a connector ring 307 of lead 301, and to further engage a connector block of a medical device in the manner discussed above. The pin 308 of the lead extends through the sleeve as discussed above, and exterior sealing rings 310 provide a fluid-tight fit with the medical device. Interior sealing rings 312 and 313 provide a fluid-tight fit with lead 301. Additional inner sealing rings (not shown) are provided to engage the proximal end of the lead as discussed above.

In this embodiment, pacing and sensing of a patient may be accomplished via ring connector 306 and pin 308 connector, which coupled to tip and ring electrodes (not shown in FIG. 8), respectively, at the lead tip. Further assume the lead carries a high-voltage coil electrode that is electrically coupled to ring connector 306. The additional bifurcation 320 may then be used to provide a connector for cardioversion/defibrillation purposes. A high-voltage defibrillation coil 322 connects conductive ring member 306 with a connector pin 324 that may conform to a second standard such as a DF-1 standard. This connector pin 324 may be utilized by a medical device to deliver a cardioversion/defibrillation shock that is then carried via coil 322 and conductive ring member 306 to conductor ring 307, and finally to the defibrillation coil electrode as the proximal end of the lead. This embodiment of the sleeve thereby allows a bipolar lead having a pace/sense electrode pair and a single shock coil to be adapted to both IS-1 and DS-1 connector blocks without the need to slit or split a catheter that is used during lead delivery. Additionally, the current inventive sleeve eliminates the pocket bulk associated with traditional longitudinal adaptors.

Sleeve 300 may be formed of one or more biocompatible polymers. For example, the hub portion 330 of the bifurcated sleeve could be formed of a more rigid material such as polyurethane that provides additional support to the structure and to the proximal end of the lead. The remainder of the sleeve, including the portions of the bifurcations 302 and 320 that include the exterior sealing rings 310 and 326, could be formed of a less rigid material such as silicone.

As noted above, the current inventive up-sizing sleeve is, in its preferred embodiment, designed to allow a lead to conform to a predetermined connector standard. For this reason, it is important that the sleeve does not stretch or deform in any manner. To provide a structure that maintains precise dimensions, more rigid support structures formed of a material such as polyurethane may be incorporated into the sleeve. The inclusion of additional sealing grommets may also be desirable to ensure both a fluid-tight seal, and the retention of predetermined sleeve dimensions.

Figure 9:
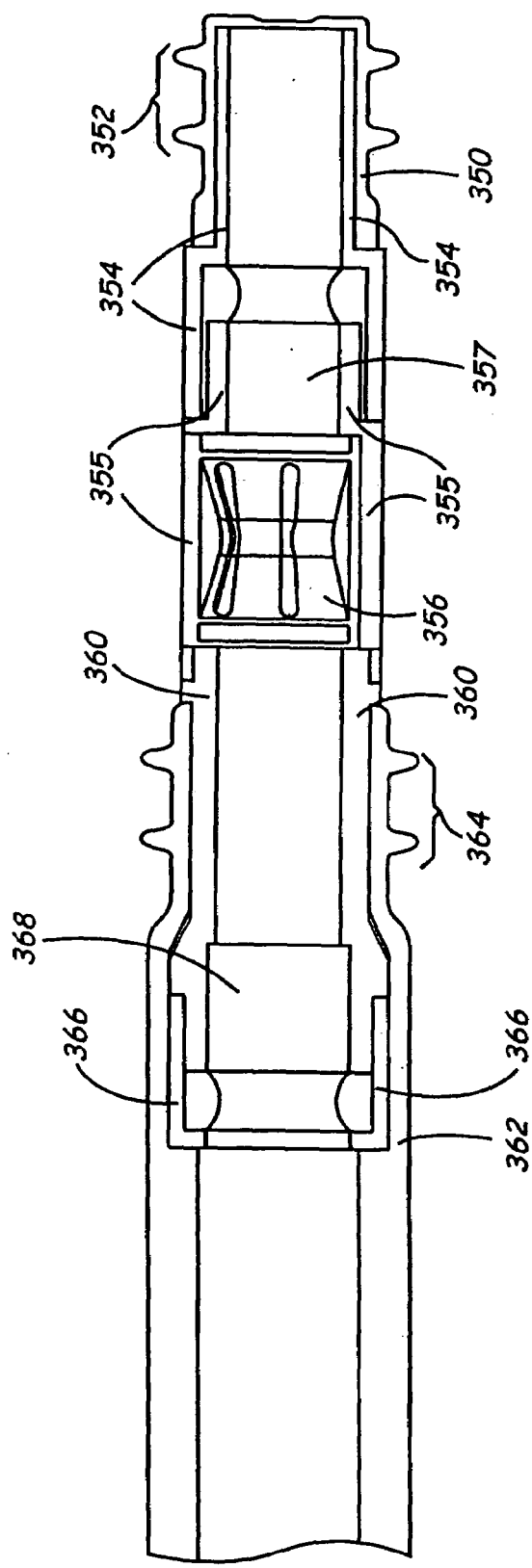
FIG. 9 is a side cutaway view of another embodiment of the current invention that incorporates both support structures and sealing grommets.

FIG. 9 is a side cutaway view of another embodiment of the current inventive up-sizing sleeve that incorporates both support structures and sealing grommets. A first, less-rigid tubular sleeve member 350 is shown having exterior sealing rings 352 as discussed above. Tubular member 350, which may be formed of a silicone, is bonded to a more rigid tubular support member 354, which may be formed of polyurethane. Support member 354, is, in turn, coupled at one end to an exterior conductive ring 355 formed of an electrically-conductive material that is adapted to make an electrical connection with a connector block of a medical device, as is provided by a standard IS-1 connector.

Conductive ring 355 houses, and is mechanically and electrically coupled to, a connector member 356 that is also formed of a conductive material. Connector member 356 is adapted to make an electrical and mechanical connection with a connector ring of a lead in a manner similar to that discussed above. Connector member 356 is shown in this embodiment to be a multi-beam connector having deformable fingers adapted to form a press-fit with a lead connector ring. Alternatively, connector member 356 may take the form of any other type of connector known in the art, including any of the types of connectors discussed above.

Housed within conductive ring 354 may be a sealing grommet 357 provided to form a superior fluid-tight seal with a lead. Sealing grommet 357 may be formed of a more deformable material such a silicone, for example.

Conductive ring 355 is further bonded or welded to a second rigid tubular support member 360, which may be formed of polyurethane or a metal. This second tubular support member 360 is also mechanically coupled to a less rigid, tubular sleeve member 362 having sealing rings 364, and which may be formed of silicone. Tubular support member 360 is bonded to a lip member 366 adapted to house a second sealing grommet 368. Lip member 366 may be formed of a rigid polymer such as a polyurethane, whereas the sealing grommet may be formed of silicone.

The embodiment shown in FIG. 9 provides a more flexible design. The length of the sealing grommets may be adjusted to position the conductive ring 355 based on a selected connector standard. Moreover, the multi-beam connector shown as connector member 356 may be adjusted to couple to any lead size requirement. This design is adaptable for over-the-wire leads, and small coil-over-cable leads having an outer diameter of 5 French or less.

It may be noted that while the multi-beam connector 356 of FIG. 9 may be adapted to form an electrical connection with a connector ring of a multi-polar lead, this need not be the case. In one embodiment, the multi-beam connector 356 may be formed of a non-conductive material. In this case, the connector 356 is adapted to form a mechanical connection with a unipolar lead so that the lead body is maintained in a stable position with respect to the up-sizing sleeve. In this embodiment, conductive ring 355 may be omitted if desired, or a similar structure may be provided that is formed of a non-conductive material.

Figure 10A:
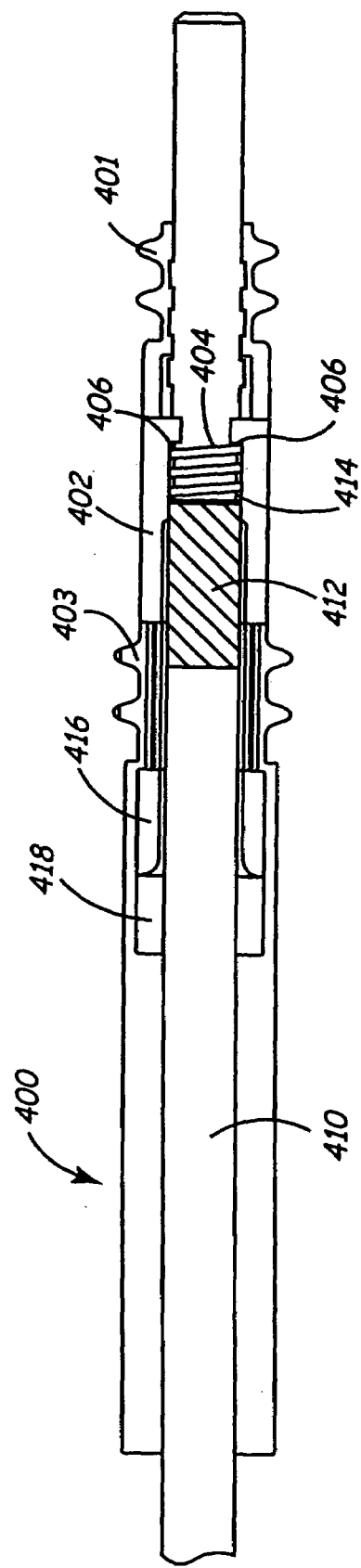
FIG. 10A is a side cutaway view showing an embodiment of the up-sizing sleeve that includes a spring coil to form the electrical connection between a lead ring is connector and a conductive ring member of the upsizing sleeve.

FIG. 10A is a side cutaway view showing yet another embodiment of the up-sizing sleeve that includes a spring coil to form the electrical connection between a lead ring connector and a conductive ring member of the upsizing sleeve 400. Up-sizing sleeve 400 includes many of the components described above with respect to other ones of the embodiments of the invention. For example, the embodiment of FIG. 10A includes flexible tubular members 401 and 403, which may be formed of a silicone, and which are coupled as with a medical-grade adhesive to an electrically-conductive ring member 402. Most notably, in this embodiment conductive ring member 402 is electrically and mechanically coupled at one end to a deformable spring coil 404. Spring coil 404, which is formed of an electrically-conductive material, may be spot welded or otherwise coupled to a shoulder 406 of conductive ring member 402. In this embodiment, lead 410 includes a ring conductor 412 having a lip 414 to engage spring coil 404. In this manner, ring connector 412 is electrically coupled to the conductive ring member 402, which, in turn, may be coupled to the connector block of a medical device. The upsizing sleeve may further include one or more grommets such as grommet 416, which is maintained in position by a polyurethane lip member 418 similar to that shown in the embodiment of FIG. 9. The upsizing sleeve may further include other aspects described with respect to the embodiments of FIGS. 1-9 as would be apparent to those skilled in the art.

Figure 10B:
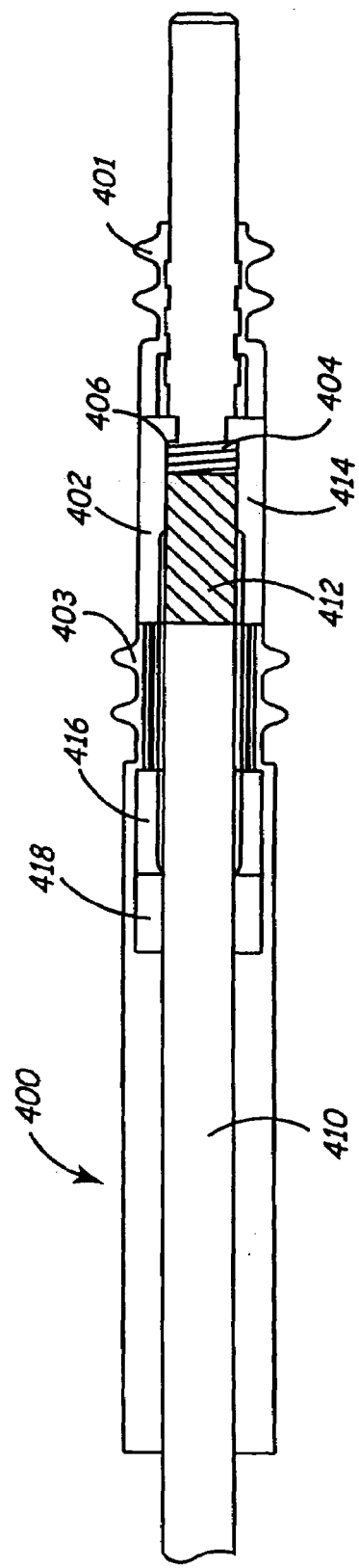
FIG. 10B is a side cutaway view of the embodiment of FIG. 10A illustrating the manner in which the spring coil compresses when the lead is fully inserted within the up-sizing sleeve.

FIG. 10B is a side cutaway view of the embodiment of FIG. 10A illustrating the manner in which the spring coil 404 compresses when the lead is fully inserted within the up-sizing sleeve 400.

Figure 11A:
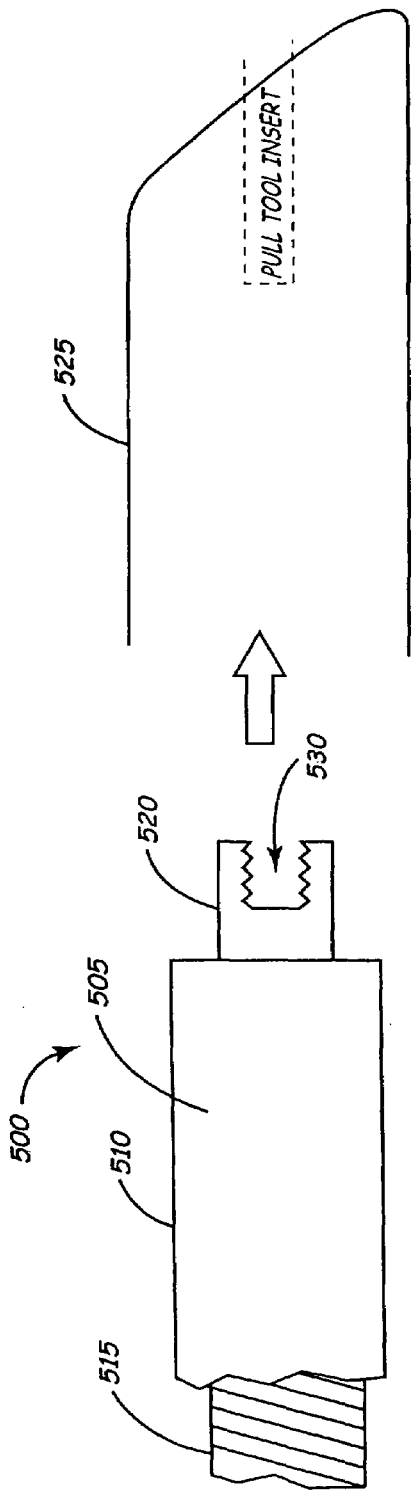
FIG. 11A is a side view perspective of a lead connector arrangement including a non-cylindrically shaped connector pin and connector sleeve assembly in accordance with one embodiment of the present invention.

FIG. 11A illustrates a lead connector arrangement 500 in accordance with one embodiment of the present invention. A lead body 505 is formed of a length of outer insulating sheath 510 having proximal and distal ends and a sheath lumen. The sheath 510 operates as an electrical insulator, and, in one embodiment, is formed of a bio-compatible silicone rubber or polyurethane compound, which is substantially inert to body fluids. A single filar or multi-filar coiled wire conductor 515 having a coil lumen formed therein is loosely received within the sheath lumen of the sheath 510 of the lead body 505. The coiled wire conductor 515 and a connector pin 520 are receivable within a connector sleeve assembly 525 for coupling the lead body 505 to an implantable medical device via the connector sleeve assembly 525. The connector pin 520 is further configured with an inner threaded recess 530 within its tip to receive a threaded pull-wire device (as illustrated in FIG. 2A).

Typically, if the pull-wire device is over-tightened (clockwise) within the inner threaded recess of a connector pin (prior to being pulled into the connector sleeve assembly), it may be difficult to unscrew the pull-wire device (counterclockwise) from the connector pin of the coiled wire conductor without causing axial rotation of the coiled wire conductor within the connector sleeve assembly. That is, because conventionally the connector pin takes the form of a cylindrical shape, it may rotate within the connector sleeve assembly when the pull-wire device is unscrewed from the inner threaded recess of the connector pin. If such axial rotation of the coiled wire conductor occurs, it may provide enough torque on the coiled wire conductor such that the torque may transfer to the electrode tip which is coupled to a distal portion of the coiled wire conductor and that is implanted within the patient's heart. Accordingly, it is possible that the electrode tip may undesirably become displaced or dislodged from the patient's heart as a result of this axial rotation on the coiled wire conductor. If the electrode tip becomes displaced or dislodged, the entire implantation process of the catheter-delivered electrical lead would need to be repeated, thereby resulting in additional time, costs and/or physical trauma to the patient.

In accordance with the illustrated embodiment, the connector pin 520 is non-cylindrically shaped to fit within a corresponding molded form insert within the connector sleeve assembly 525 so as to reduce the likelihood of axial rotation of the coiled wire conductor 515 when the pull-wire device 110 is unscrewed from an inner threaded recess 530 of the non-cylindrically shaped connector pin 520.

Figure 11B:
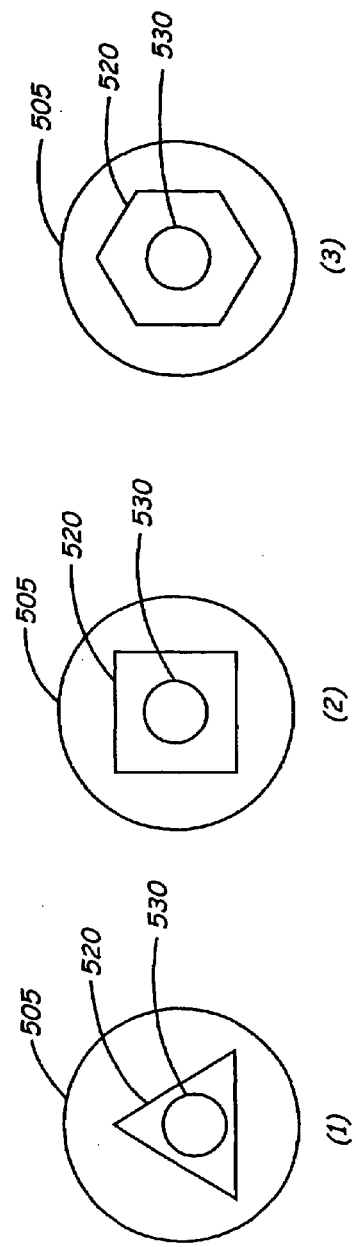
FIG. 11B is a front view perspective of various non-cylindrically shaped connector pins of the lead connector arrangement of FIG. 11A.

In accordance with one embodiment of the present invention, the connector pin 520 may be provided in the form of a triangular-shaped tip as shown in FIG. 11B (1), which provides a front view perspective of the connector pin 520 looking down the lead body 505 from the tip of the connector pin 520. In an alternative embodiment, the connector pin 520 may take the form of a square or rectangular-shaped tip as illustrated in FIG. 11B (2). In yet another embodiment, the connector pin 520 may take the form of a hexagonal-shaped tip as shown in FIG. 11B (3).

Figure 11C:
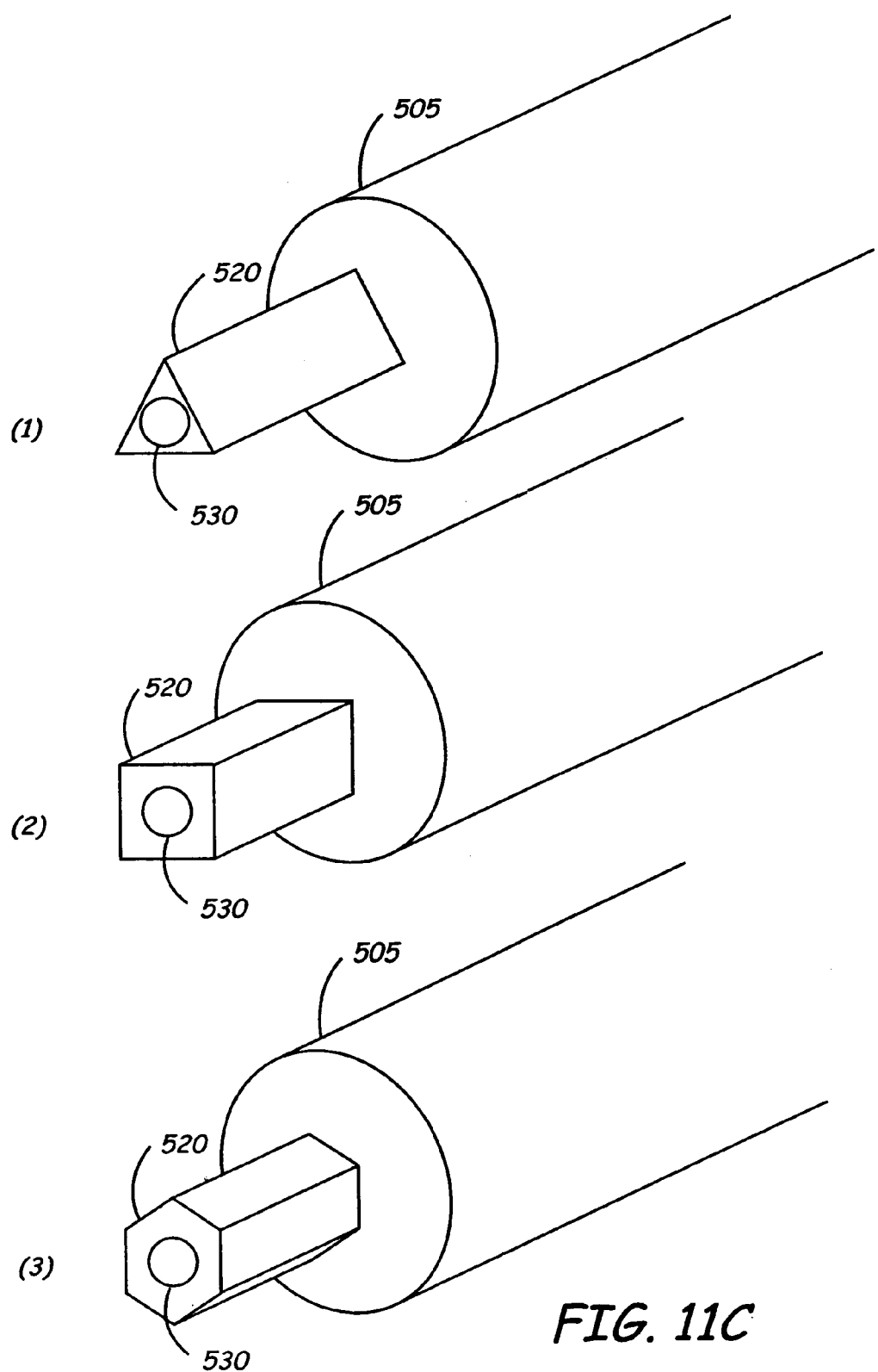
FIG. 11C is a side view, three-dimensional perspective of the non-cylindrically shaped connector pins of FIG. 11 B.

FIG. 11C (1)-(3) shows a corresponding, three-dimensional perspective side view of the non-cylindrically shaped connector pins 520 as are respectively illustrated in FIG. 11B (1)-(3). The connector pins 520 illustrated in FIGS. 1B and 11C provide only a few examples of non-cylindrically shaped tips that the connector pin 520 may take. Accordingly, it will be appreciated that the connector pin 520 may take the form of any other shaped tip having edges and surfaces that may be retained within a molded insert of a lead without departing from the spirit and scope of the present invention. For example, the tip of the connector pin 520 may take the form of a pentagonal shape, a heptagonal shape, an octagonal shape, etc. The connector pin 520 may be provided with one or more planar (flat) surfaces, along with curved surfaces, to reduce axial rotation.

FIG. 11D illustrates the lead body 505 as being fully disposed within the connector sleeve assembly 525. According to the illustrated embodiment, the connector sleeve assembly 525 is configured with a molded form insert 535 with an axial bore (or connector bore) 540 that complements the non-cylindrical shape of the connector pin 520. Accordingly, if the connector pin 520 is provided in the form of a triangular shape (as illustrated in FIGS. 11B and C), the axial bore 540 of the molded form insert 535 within the connector sleeve assembly 525 would take the form of a triangular shaped socket to receive the triangular shaped connector pin 520. Similarly, if the connector pin 520 takes the form of a square or rectangular shaped tip, the axial bore 540 of the molded form insert 535 would take the form of a complementary square or rectangular shaped socket to accommodate the insertion of the connector pin 520 within the connector sleeve assembly 525.

FIG. 11E provides a front perspective view of the molded form insert 535, with the axial bore 540 formed therein, which is disposed within the connector sleeve assembly 525. The axial bore 540 within the molded form insert 535 receives a complementary shaped (e.g., triangular, rectangular, etc.) connector pin 520 to prevent axial rotation of the coiled wire conductor 515 when the connector pin 520 is fully inserted within its corresponding axial bore 540 of the molded form insert 535.

In accordance with this particular embodiment, the pull-wire device 110 is inserted through the connector sleeve assembly 525 at the pull-wire insertion site (as designated in FIGS. 11A and 11D). The pull-wire device 110 is then screwed into the inner threaded recess 530 of the connector pin 520. The connector pin 520, and the coiled wire conductor 515 coupled thereto, is then pulled into the connector sleeve assembly 525 until the connector pin 520 is inserted as far as possible within the connector sleeve assembly 525. The pull-wire device 110 is then rotated counter-clockwise, while it is simultaneously pulled, until the non-cylindrically shaped connector pin 520 locks into the axial bore 540 of the molded form insert 535 within the connector sleeve assembly 525.

The amount of rotation of the pull-wire device 110 (such that the connector pin 520 will fit within the axial bore 540) depends upon the shape of the connector pin 520. For example, the maximum amount of rotation within the connector sleeve assembly 525 for a triangular-shaped connector pin 520 would be 120 degrees such that the orientation of the connector pin 520 would match the orientation of the complementing axial bore 540 of the molded form insert 535 within the connector sleeve assembly 525. On the other hand, the maximum amount of rotation for a hexagonal-shaped connector pin 520 by the pull-wire device 110 would be 60 degrees. For polygonal shaped connector pins 520 having a number of sides greater than six, the potential for rotation of the connector pin 520 would be less than 60 degrees.

Subsequent to mating the connector pin 520 within the axial bore 540 of the molded form insert 535, the pull-wire device 110 may be unscrewed from the inner threaded recess 530 of the connector pin 520 without axial rotation of the coiled wire conductor 515 occurring within the connector sleeve assembly 525.

Figure 12A:
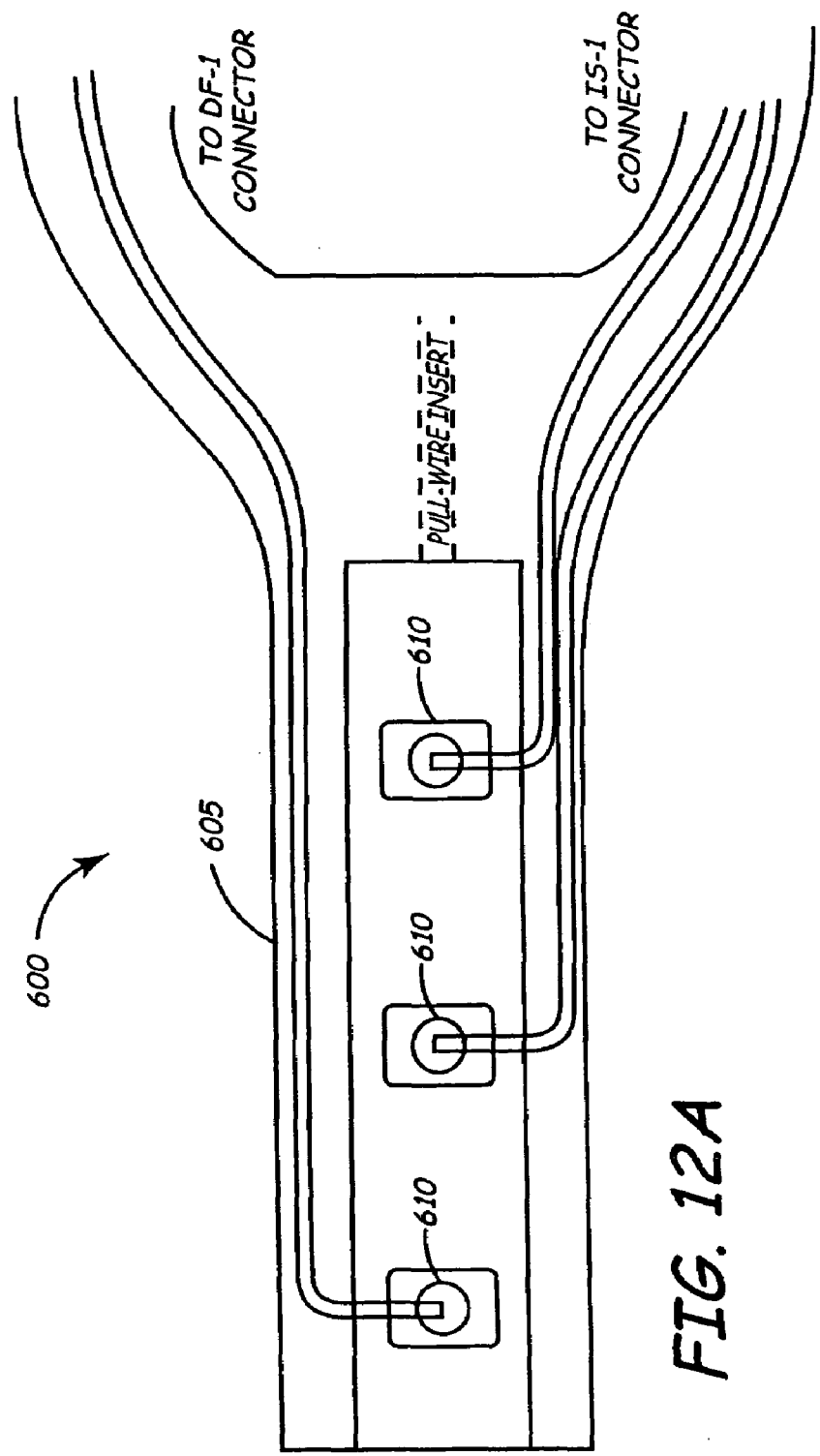
FIG. 12A is a side view perspective of a lead connector arrangement including an adapter block assembly for receiving a non-cylindrical shaped connector pin in accordance with another embodiment of the present invention.

FIG. 12A illustrates a lead connector arrangement 600, which includes a bifurcated adapter block 605 for receiving the non-cylindrically shaped connector pin 520 (as illustrated in FIGS. 11B and 11C) in accordance with another embodiment of the present invention. According to the illustrated embodiment, the bifurcated adapter block 605 takes the form of an IS-1/DF-1 ICD adapter for coupling to a DF-1 connector pin standard and to an IS-1 connector pin standard. It will be appreciated, however, that the adapter block 605 may conform to other types of connector standards, in addition to the examples provided above, without departing from the spirit and scope of the present invention.

In the illustrated embodiment, the adapter block 605 is constructed of silicon rubber; however, it will be appreciated that other materials may be used in lieu thereof. The bifurcated adapter block 605 is further configured with a plurality of set screws 610 for coupling to the coiled wire conductor 515 of the lead body 505, which is received within the adapter block 605. The pull-wire device 110 is inserted into the adapter block 605 at the pull-wire insert site (as designated in FIG. 12A) to pull the lead body 505 into the adapter block 605.

Figure 12B:
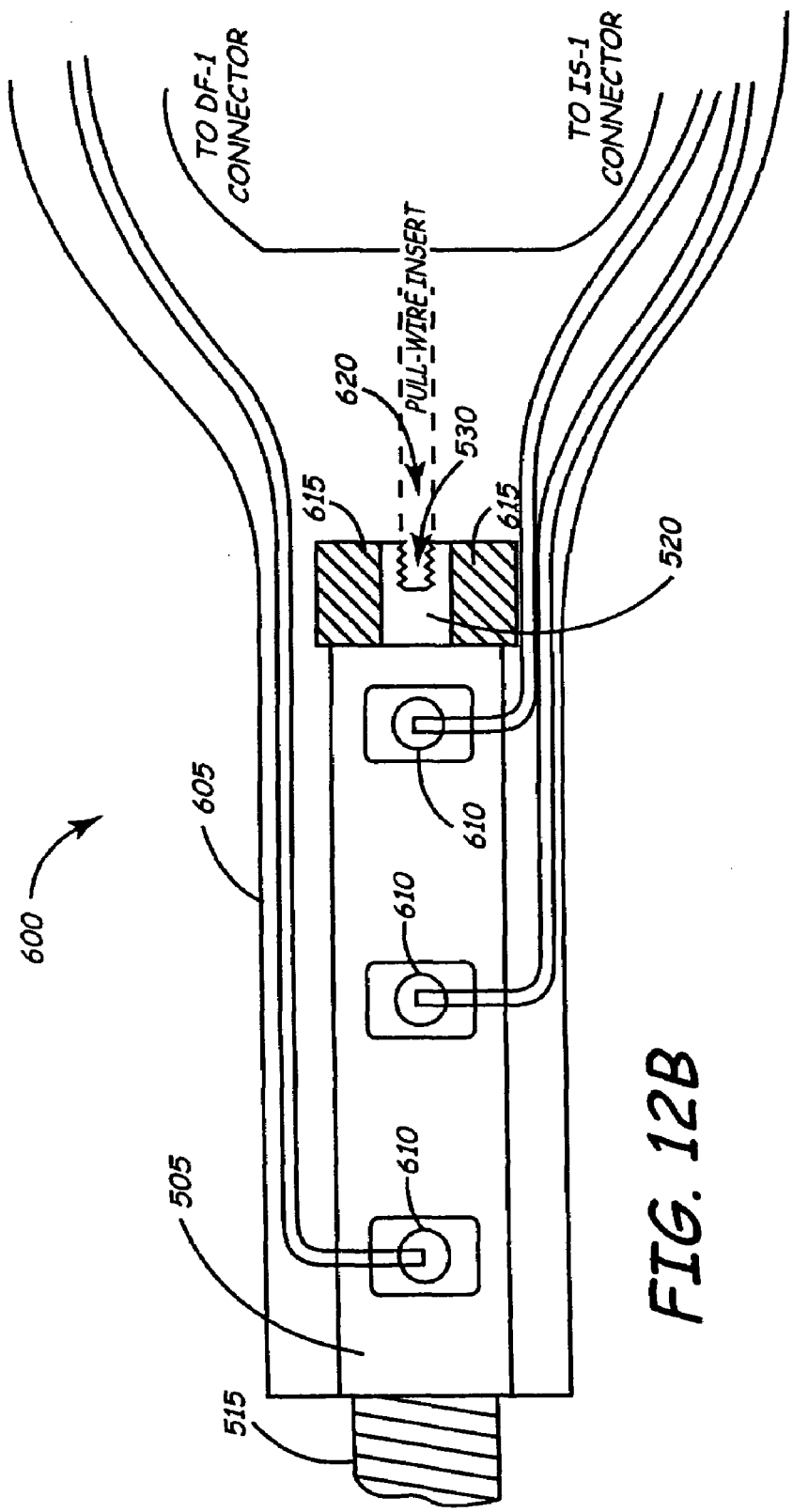
FIG. 12B is a side view perspective of the adapter block assembly of FIG. 12A with the non-cylindrical connector pin fully inserted therein.
Figure 12C:
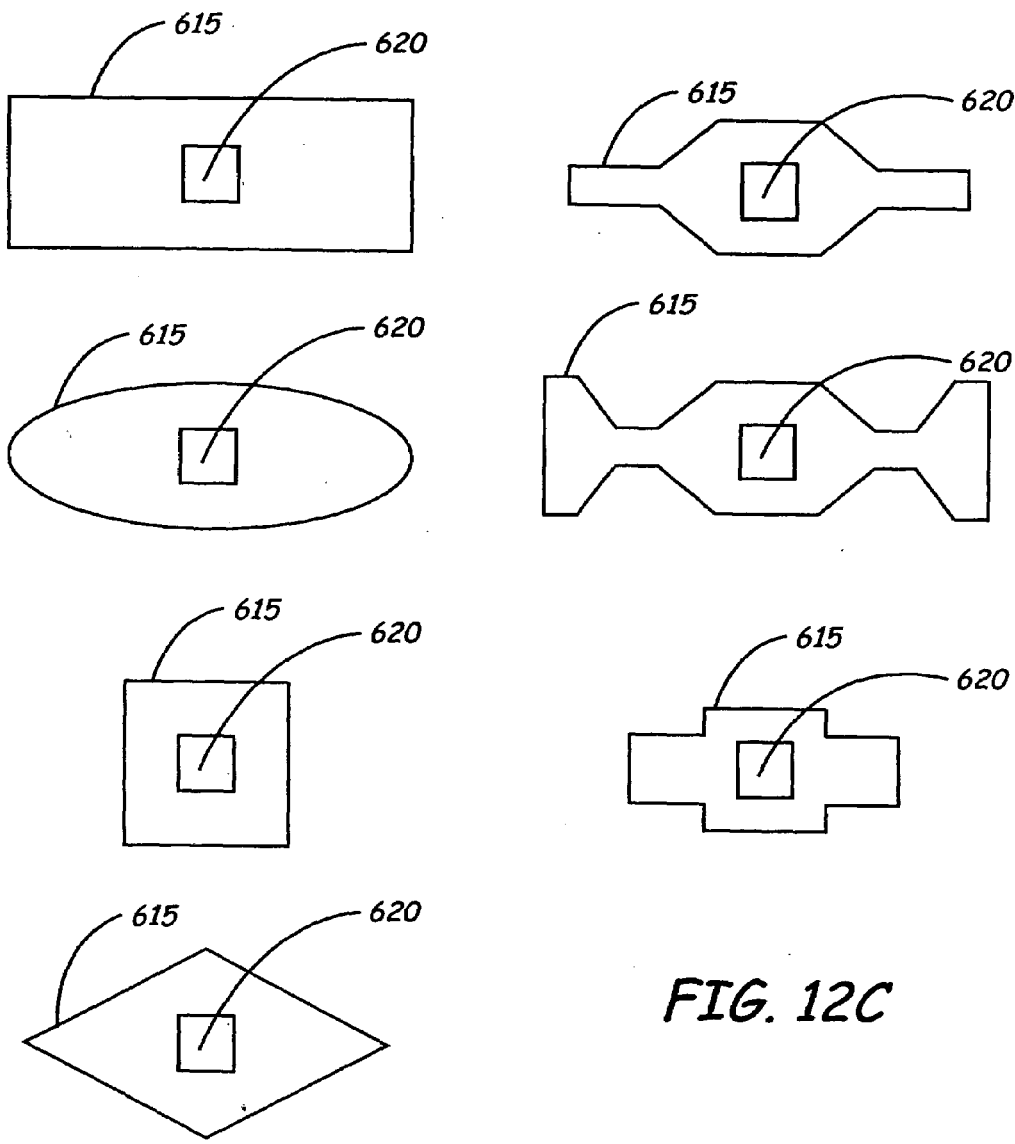
FIG. 12C is a front view perspective of various molded form inserts that may be disposed within the adapter block assembly of FIG. 12A.

Referring to FIG. 12B, the bifurcated adapter block 605 is shown with the lead body 505 fully disposed within its cavity. According to the illustrated embodiment, the adapter block 605 is provided with a molded form insert 615 having an axial bore 620 that is shaped to compliment the shape of the non-cylindrical connector pin 520. In one embodiment of the present invention, the connector pin 520 may take the form of a triangular, square, rectangular, or hexagonal shaped tip as illustrated in FIGS. 11B and 11C. It will be appreciated, however, that the connector pin 520 may take the form of various other shaped tips in addition to the examples provided. The molded form insert 615 may be provided in various shapes as illustrated in FIG. 12C, which provides a cross-sectional view of the molded form insert 615 from either side of the adapter block 605 of FIG. 12B. As shown in FIG. 12C, the various molded form inserts 615 are provided with an axial bore 620 to accommodate a square-shaped connector pin 520. It will be appreciated, however, that the axial bore 620 of the various molded form inserts 615 may be designed to accommodate a triangular, rectangular, hexagonal, or other polygonal shaped connector pin 520. Additionally, it will also be appreciated that various other shapes of the molded form inserts 615 may be used, in addition to the examples shown in FIG. 12C, without departing from the spirit and scope of the present invention. Furthermore, it will be appreciated that the adapter block assembly 605 may be provided in the form of a trifurcated adapter block assembly as illustrated in FIG. 12D, as opposed to the bifurcated adapter block as provided in FIG. 12B, without departing from the spirit and scope of the present invention.

In accordance with the illustrated embodiment, the pull-wire device 110 is inserted into the adapter block 605 at the pull-wire insert site (as designated in FIG. 12B) to pull the lead body 505 into the cavity of the adapter block 605. The pull-wire device 110 is screwed (clockwise) into the inner threaded recess 530 of the non-cylindrically shaped connector pin 520. The lead body 505 is then pulled into the cavity of the adapter block 605 using the pull-wire device 110. The pull-wire device 110 is turned counterclockwise and simultaneously pulled until the connector pin 520 locks into the axial bore 620 of the molded form insert 615 of the adapter block 605. The pull-wire device 110 may then be unscrewed from the connector pin 520 of the lead body 505 without any axial rotation of the coiled wire conductor 515 within the cavity of the adapter block 605, thereby reducing the likelihood of any lead electrode dislodgement from the patient's heart.

Figure 13A:
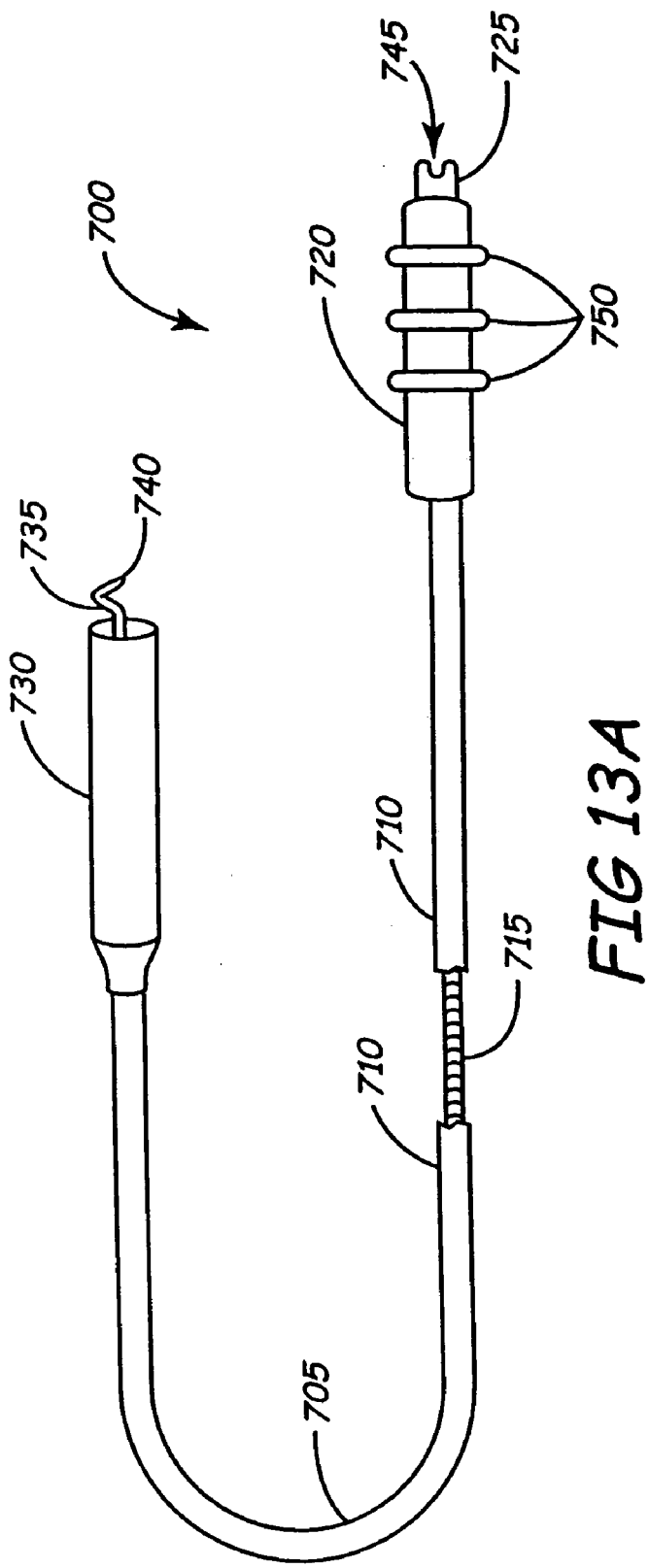
FIG. 13A is a plan view of a lead connector arrangement usable with an extendable/retractable helix in accordance with one embodiment of the present invention.

FIG. 13A illustrates a lead connector arrangement 700 in accordance with another embodiment of the present invention. A lead body 705 is formed of a length of outer insulating sheath 710 having proximal and distal ends and a sheath lumen. The sheath 710 operates as an electrical insulator. In one embodiment, sheath 710 is formed of a bio-compatible silicone rubber or polyurethane compound, which is substantially inert to body fluids. A single filar or multi-filar conductor 715 is housed within the sheath 710. The sheath 710 and conductor 715 extend between connector pin 725 and a lead electrode 730. In this embodiment, the electrode is an extendable/retractable helix 735 for affixing to the endocardium of the patient's heart. FIG. 13A further illustrates connector sleeve assembly 720 having been attached to the connector of the lead. Connector sleeve assembly 720 may take the form of any of the embodiments previously described above.

During an implant procedure, a lead such as shown in FIG. 13A is advanced into the body, and the helix is affixed to tissue as is known in the art. Generally, the process of affixing the helix will involve rotating the connector pin 725 of the lead in a clockwise direction. This motion will, in turn, rotate conductor 715, as well as helix 735, which is electrically and mechanically coupled to the conductor.

Next, the connector portion of the lead may be pulled into the connector sleeve assembly. This involves attaching the pullwire device 110 (FIG. 2A) to inner threaded recess 745 by rotating the pullwire device 110 in a clockwire direction. Although this may impart clockwise rotation to connector pin 725, this has no effect on the helix extension since the helix is already in a fully extended position.

Next, the pullwire device 110 is used to pull the connector pin 725 through the lumen of the connector sleeve assembly 720. When the lead connector is properly seated within the connector sleeve assembly, the pullwire device 110 may be removed by rotating the pullwire device in a counter clockwise direction. This action may impart counter clockwise rotation to the connector pin 725, causing the helix to become detached from tissue, as discussed above. However, the current invention prevents such detachment by providing a structure within the connector sleeve assembly that locks to, and prevents rotation of, the connector pin 725.

Figure 13C:
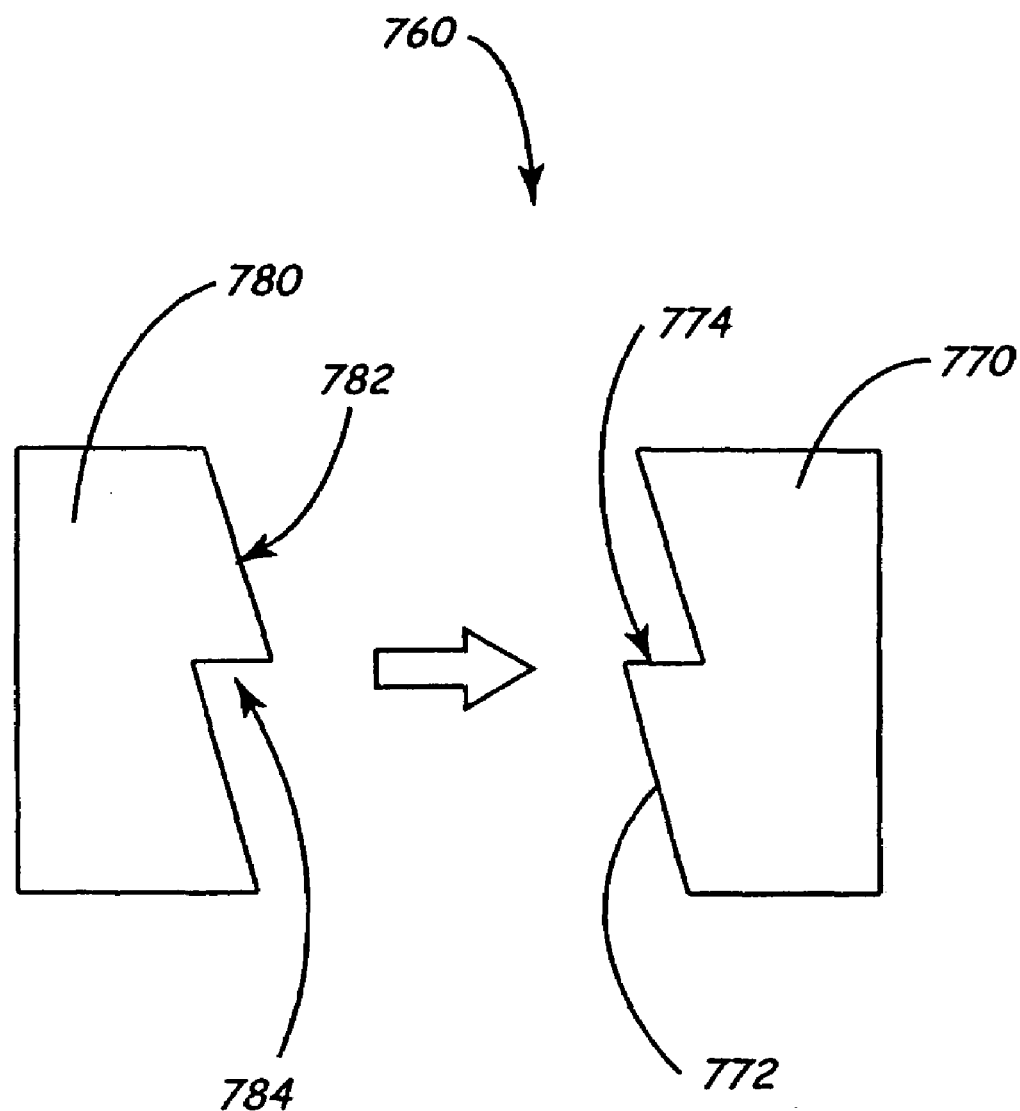
FIG. 13C is a side view perspective of a retraction stop mechanism within the connector sleeve assembly of FIG. 13B.

FIG. 13B provides a more detailed representation of the connector sleeve assembly 720. In accordance with the illustrated embodiment, a retraction stop mechanism 760 is provided within the connector sleeve assembly 720 to prevent axial rotation of the coiled wire conductor 715 when the pull-wire device 110 is being unscrewed from the connector pin 725, thereby preventing the helix 735 from the lead electrode 730 from being retracted. The retraction stop mechanism 760 comprises a fixed stop 770 that is attached to the inner cavity of the connector sleeve assembly 720. Referring to FIG. 13C, the fixed stop 770 comprises a plurality of fixed cam 772 and axial stop 774 surfaces in a "ring" configuration surrounding the inner chamber of the connector sleeve assembly 720 through which the coiled wire conductor 715 extends. In accordance with one embodiment, the fixed stop 770 may include four fixed cam stop surfaces 772 and four axial stop surfaces 774 that are equidistantly disposed along the "mating" surface of the fixed stop 770. It will be appreciated, however, that the number of fixed cam stop and axial stop surfaces 772, 774 may include a greater or fewer number than the example provided without departing from the spirit and scope of the present invention.

In one embodiment, the retraction stop mechanism 760 may further be configured with a movable stop 780 that is affixed to the outer surface of the coiled wire conductor 715. The movable stop 780 also includes the same number of complementary rotatable cam 782 and axial stop 784 surfaces as the fixed cam 772 and axial stop 774 surfaces of the fixed stop 770 with which the movable stop 780 is designed to mate.

When the connector pin 725 and the coiled wire conductor 715 is pulled through the connector sleeve assembly 720 with the pull-wire device 110, the retraction stop mechanism 760 causes the fixed stop 770 within the connector sleeve assembly 720 to engage or "lock" with the movable stop 780 of the coiled wire conductor 715. That is, when the connector pin 725 is fully extended through the connector sleeve assembly 720 by the pull-wire device 110, the fixed cam 772 and axial stop 774 surfaces of the fixed stop 770 mate with the rotatable cam 782 and axial stop 784 surfaces of the movable stop 780 on the outer surface of the coiled wire conductor 715, thus preventing counter-clockwise rotation of the coiled wire conductor 715 when the pull-wire device 110 is unscrewed from the inner threaded recess 745 of the connector pin 725. Accordingly, the extendable/retractable helix 735 within the lead electrode 730 is substantially unaffected by the disengagement of the pull-wire device 110 from the connector pin 725.

It may be noted that the inventive system and method of coupling a lead to a medical device as described and illustrated herein may be adapted for use with any size lead, any type of connector standard, and any type of medical device. For example, the up-sizing sleeve may be used with leads for drug delivery devices, devices adapted for neurological applications, or for any other type of physiological application requiring a lead coupled to an implantable or non-implantable device.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of coupling a lead conductor to a device connector, comprising the steps of:
    feeding a connector pin having a non-cylindrically shaped connector pin coupled to a lead conductor into an insert with an axial bore of a connecting adapter using a pull-wire device screwed into a threaded recess in a tip of the connector pin, the axial bore having a shape that complements the shape of the connector pin; and
    unscrewing the pull-wire device from the threaded recess of the connector pin tip without causing axial rotation of the lead connector pin due to resistance provided between the non-cylindrically shaped connector pin and the complementary shaped axial bore of the connecting adapter insert.

2. The method of claim 1, wherein a non-cylindrically shaped connector pin comprises:
    a polygonal shaped connector pin coupled to a lead conductor.

3. The method of claim 2, wherein a polygonal shaped connector pin
    is of a configuration selected from a group consisting of a triangular, square, rectangular, and hexagonal shaped connector pin.

4. The method of claim 1, wherein the connecting adapter comprises an adapter block assembly capable of connecting the lead conductor to at least two types of connector standards.

5. A lead connector arrangement, comprising:
    a lead having a non-cylindrically shaped connector pin coupled to a lead conductor; and
    an adapter block assembly for receiving the connector pin within a cavity formed therein, the adapter block assembly comprising a bifurcated adapter block having a first adapter capable of connecting the lead conductor in accordance with a first connector pin standard and a second adapter capable of connecting the lead conductor in accordance with a second connector pin standard;
    wherein the adapter block assembly includes an insert with an axial bore formed therein within the cavity that complements the shape of the connector pin.

6. The lead connector arrangement of claim 5, wherein the non-cylindrically shaped connector pin comprises at least one planar surface.

7. The lead connector arrangement of claim 5, wherein the non-cylindrically shaped connector pin comprises a polygonal shaped connector pin.

8. The lead connector arrangement of claim 7, wherein the polygonal shaped connector pin comprises at least one of a triangular, square, rectangular, and hexagonal shaped connector pin.

9. The lead connector arrangement of claim 5, wherein the lead connector arrangement couples the lead conductor to an implantable medical device.

* * * * *